(12) United States Patent
Keren et al.

(10) Patent No.: US 10,617,322 B2
(45) Date of Patent: *Apr. 14, 2020

(54) SYSTEM, METHOD AND APPARATUS FOR MEASURING BLOOD FLOW AND BLOOD VOLUME

(71) Applicant: Cheetah Medical, Inc., Wilmington, DE (US)

(72) Inventors: Hanan Keren, Kfar-Saba (IL); Avram B. Simon, London (GB)

(73) Assignee: Cheetah Medical, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/757,920

(22) Filed: Feb. 4, 2013

(65) Prior Publication Data

US 2013/0144177 A1 Jun. 6, 2013

Related U.S. Application Data

(62) Division of application No. 11/884,227, filed as application No. PCT/IL2006/000075 on Jan. 18, 2006, now Pat. No. 8,388,545.

(60) Provisional application No. 60/652,773, filed on Feb. 15, 2005.

(51) Int. Cl.
*A61B 5/026* (2006.01)
*A61B 5/0295* (2006.01)
*A61B 5/053* (2006.01)
*A61B 5/00* (2006.01)

(52) U.S. Cl.
CPC ............ *A61B 5/0535* (2013.01); *A61B 5/026* (2013.01); *A61B 5/0295* (2013.01); *A61B 5/7239* (2013.01)

(58) Field of Classification Search
CPC ...... A61B 5/0535; A61B 5/026; A61B 5/7239; A61B 5/0295
USPC ................... 600/504, 481; 330/135
See application file for complete search history.

(56) References Cited

U.S. PATENT DOCUMENTS

| 3,340,867 | A | | 9/1967 | Kubicek et al. |
| 3,605,723 | A | | 9/1971 | King et al. |
| 3,851,641 | A | | 12/1974 | Toole et al. |
| 3,871,359 | A | | 3/1975 | Pacela |
| 3,874,368 | A | * | 4/1975 | Asrican ............... A61B 5/7239 600/526 |
| 3,914,999 | A | * | 10/1975 | Grandchamp ............ 73/861.25 |

(Continued)

FOREIGN PATENT DOCUMENTS

| EP | 1247487 | 10/2002 |
| EP | 2146630 | 1/2010 |

(Continued)

OTHER PUBLICATIONS

Official Action dated Jun. 26, 2013 From the US Patent and Trademark Office Re. U.S. Appl. No. 12/527,697.

(Continued)

*Primary Examiner* — Navin Natnithithadha

(57) ABSTRACT

A method of calculating blood flow in an organ of a subject using output radiofrequency signals transmitted to the organ and input radiofrequency signals received from the organ, the method comprises determining a phase shift of the input radiofrequency signals relative to the output radiofrequency signals and using the phase shift to calculate the blood flow in the organ.

9 Claims, 20 Drawing Sheets

(56) References Cited

U.S. PATENT DOCUMENTS

| | | | |
|---|---|---|---|
| 3,976,052 A * | 8/1976 | Junginger | A61B 5/0245 600/484 |
| 4,094,309 A | 6/1978 | Grzenia | |
| 4,153,048 A | 5/1979 | Magrini | |
| RE30,101 E | 9/1979 | Kubicek et al. | |
| 4,391,148 A * | 7/1983 | Sainz | G01F 1/663 604/915 |
| 4,437,469 A * | 3/1984 | Djordjevich | A61B 5/0535 600/485 |
| 4,450,527 A | 5/1984 | Sramek | |
| 4,537,200 A | 8/1985 | Widrow | |
| 4,610,254 A | 9/1986 | Morgan et al. | |
| 4,705,049 A | 11/1987 | John | |
| 4,781,201 A | 11/1988 | Wright et al. | |
| 4,803,431 A | 2/1989 | Sano et al. | |
| 4,805,621 A | 2/1989 | Heinze et al. | |
| 4,852,580 A | 8/1989 | Wood | |
| 4,870,578 A * | 9/1989 | Vysin | A61B 5/0456 600/484 |
| 4,888,558 A | 12/1989 | Hereikson | |
| 4,926,868 A | 5/1990 | Larsen | |
| 4,953,556 A | 9/1990 | Evans | |
| 5,058,583 A | 10/1991 | Geddes et al. | |
| 5,158,093 A | 10/1992 | Shvartz et al. | |
| 5,178,154 A | 1/1993 | Ackman et al. | |
| 5,309,917 A | 5/1994 | Wang et al. | |
| 5,316,004 A | 5/1994 | Chesney et al. | |
| 5,423,326 A | 6/1995 | Wang et al. | |
| 5,469,859 A | 11/1995 | Tsoglin et al. | |
| 5,503,157 A | 4/1996 | Sramek | |
| 5,505,209 A | 4/1996 | Reining | |
| 5,529,072 A | 6/1996 | Sramek | |
| 5,615,689 A | 4/1997 | Kotler | |
| 5,642,734 A * | 7/1997 | Ruben | A61B 5/14535 600/506 |
| 5,685,316 A | 11/1997 | Shookin et al. | |
| 5,817,030 A | 10/1998 | Tarjan et al. | |
| 5,913,826 A | 6/1999 | Blank | |
| 6,015,393 A | 1/2000 | Hovland et al. | |
| 6,053,873 A | 4/2000 | Govari et al. | |
| 6,073,039 A | 6/2000 | Berson | |
| 6,076,015 A | 6/2000 | Hartley et al. | |
| 6,142,941 A | 11/2000 | Benhalima et al. | |
| 6,298,267 B1 | 10/2001 | Rosborough et al. | |
| 6,304,773 B1 | 10/2001 | Taylor et al. | |
| 6,339,722 B1 | 1/2002 | Heethaar et al. | |
| 6,413,223 B1 | 7/2002 | Yang et al. | |
| 6,440,082 B1 | 8/2002 | Joo et al. | |
| 6,485,431 B1 | 11/2002 | Campbell et al. | |
| 6,496,732 B1 | 12/2002 | Wallace | |
| 6,511,438 B2 | 1/2003 | Bernstein et al. | |
| 6,577,897 B1 | 6/2003 | Shurubura et al. | |
| D625,823 S | 10/2010 | Schneider et al. | |
| 8,388,545 B2 * | 3/2013 | Keren | A61B 5/0535 600/481 |
| 8,414,498 B2 | 4/2013 | Keren et al. | |
| 8,523,777 B2 | 9/2013 | Avidor et al. | |
| 8,764,667 B2 | 7/2014 | Avidor et al. | |
| 8,790,267 B2 | 7/2014 | Keren et al. | |
| 8,876,725 B2 | 11/2014 | Keren et al. | |
| 9,095,271 B2 * | 8/2015 | Keren | A61B 5/02028 |
| 2002/0143368 A1 | 10/2002 | Bakels et al. | |
| 2002/0193689 A1 | 12/2002 | Bernstein et al. | |
| 2003/0083702 A1 | 5/2003 | Stadler et al. | |
| 2003/0109790 A1 | 6/2003 | Stickney et al. | |
| 2003/0120170 A1 | 6/2003 | Zhu et al. | |
| 2003/0158584 A1 | 8/2003 | Cates et al. | |
| 2003/0187341 A1 | 10/2003 | Sackner et al. | |
| 2003/0199779 A1 | 10/2003 | Muhlenberg et al. | |
| 2004/0034294 A1 | 2/2004 | Kimball et al. | |
| 2004/0102908 A1 | 5/2004 | Larson et al. | |
| 2004/0133123 A1 | 7/2004 | Leonhardt et al. | |
| 2005/0004609 A1 | 1/2005 | Stahmann et al. | |
| 2005/0043763 A1 | 2/2005 | Marcovecchio et al. | |
| 2005/0113703 A1 | 5/2005 | Farringdon et al. | |
| 2005/0119586 A1 | 6/2005 | Coyle et al. | |
| 2005/0124901 A1 | 6/2005 | Misczynski et al. | |
| 2005/0143634 A1 | 6/2005 | Baker, Jr. et al. | |
| 2005/0192488 A1 | 9/2005 | Bryenton et al. | |
| 2005/0202789 A1 * | 9/2005 | Tanabe et al. | 455/110 |
| 2005/0217674 A1 | 10/2005 | Burton et al. | |
| 2006/0085048 A1 | 4/2006 | Cory et al. | |
| 2006/0094964 A1 | 5/2006 | Ragauskas et al. | |
| 2006/0122540 A1 | 6/2006 | Zhu et al. | |
| 2006/0200033 A1 | 9/2006 | Keren et al. | |
| 2007/0088221 A1 | 4/2007 | Stahmann | |
| 2007/0191688 A1 | 8/2007 | Lynn | |
| 2008/0154116 A1 | 6/2008 | Duensing et al. | |
| 2008/0255433 A1 | 10/2008 | Prough et al. | |
| 2009/0048497 A1 * | 2/2009 | Keren | A61B 5/02028 600/301 |
| 2010/0031959 A1 * | 2/2010 | Avidor | A61B 5/029 128/204.23 |
| 2010/0069765 A1 * | 3/2010 | Keren | A61B 5/0535 600/504 |
| 2010/0152600 A1 * | 6/2010 | Droitcour | A61B 5/05 600/534 |
| 2010/0191127 A1 * | 7/2010 | Keren | A61B 5/02028 600/484 |
| 2010/0217140 A1 * | 8/2010 | Avidor | A61B 5/0535 600/509 |
| 2010/0240999 A1 * | 9/2010 | Droitcour | A61B 5/05 600/453 |
| 2010/0249630 A1 * | 9/2010 | Droitcour | A61B 5/05 600/529 |
| 2010/0249633 A1 * | 9/2010 | Droitcour | A61B 5/05 600/534 |
| 2010/0292568 A1 * | 11/2010 | Droitcour | A61B 5/05 600/425 |
| 2011/0218419 A1 * | 9/2011 | Keren | A61B 5/02028 600/407 |
| 2015/0272450 A1 | 10/2015 | Keren | |

FOREIGN PATENT DOCUMENTS

| | | |
|---|---|---|
| WO | WO 82/00581 | 3/1982 |
| WO | WO 96/32883 | 10/1996 |
| WO | WO 97/11638 | 4/1997 |
| WO | WO 00/66222 | 11/2000 |
| WO | WO 2004/098376 | * 11/2004 |
| WO | WO 2004/112606 | 12/2004 |
| WO | WO 2006/087696 | 8/2006 |
| WO | WO 2007/096054 | 8/2007 |
| WO | WO 2008/102362 | 8/2008 |
| WO | WO 2008/107899 | 9/2008 |
| WO | WO 2008/129535 | 10/2008 |
| WO | WO 2009/022330 | 2/2009 |

OTHER PUBLICATIONS

Official Action dated Apr. 9, 2013 From the US Patent and Trademark Office Re. U.S. Appl. No. 12/527,697.
Official Action dated Apr. 30, 2013 From the US Patent and Trademark Office Re. U.S. Appl. No. 11/889,395.
Notice of Allowance dated Jan. 30, 2013 From the US Patent and Trademark Office Re.: U.S. Appl. No. 10/556,483.
Official Action dated Jun. 17, 2013 From the US Patent and Trademark Office Re. U.S. Appl. No. 12/450,022.
Applicant-Initiated Interview Summary dated Sep. 17, 2012 From the US Patent and Trademark Office Re. U.S. Appl. No. 11/884,227.
Communication Pursuant to Article 94(3) EPC dated Jul. 8, 2009 From the European Patent Office Re.: Application No. 04731993.4.
Communication Pursuant to Article 94(3) EPC dated Feb. 12, 2010 From the European Patent Office Re.: Application No. 08738211.5.
Communication Pursuant to Article 94(3) EPC dated Feb. 13, 2012 From the European Patent Office Re. Application No. 08719934.5.
Communication Pursuant to Article 94(3) EPC dated Feb. 13, 2012 From the European Patent Office Re. Application No. 08789780.7.
Communication Pursuant to Article 94(3) EPC dated Feb. 13, 2012 From the European Patent Office Re.: Application No. 08710233.1.

(56) References Cited

OTHER PUBLICATIONS

Communication Pursuant to Article 94(3) EPC dated May 14, 2012 From the European Patent Office Re.: Application No. 04731993.4.
Communication Pursuant to Article 94(3) EPC dated Oct. 20, 2010 From the European Patent Office Re. Application No. 08719934.5.
Communication Pursuant to Article 94(3) EPC dated Jan. 26, 2011 From the European Patent Office Re.: Application No. 04731993.4.
Communication Pursuant to Article 94(3) EPC dated Dec. 29, 2009 From the European Patent Office Re.: Application No. 08710233.1.
Communication Relating to the Results of the Partial International Search dated Dec. 5, 2008 From the International Searching Authority Re.: Application No. PCT/IL2008/001105.
Communication Under Rule 71(3) EPC dated Oct. 7, 2011 From the European Patent Office Re.: Application No. 08738211.5.
Communication Under Rule 71(3) EPC dated Oct. 17, 2012 From the European Patent Office Re. Application No. 08789780.7.
Examiner's Report dated Nov. 15, 2010 From the Australian Government, IP Australia Re. Application No. 2006215274.
International Preliminary Report on Patentability dated Nov. 4, 2009 From the International Preliminary Examining Authority Re.: Application No. PCT/IL2008/001105.
International Preliminary Report on Patentability dated Aug. 16, 2007 From the International Preliminary Examining Authority Re.: Application No. PCT/IL06/00075.
International Preliminary Report on Patentability dated Sep. 17, 2009 From the International Bureau of WIPO Re.: Application No. PCT/IL2008/000309.
International Preliminary Report on Patentability dated Nov. 18, 2008 From the International Preliminary Examing Authority Re.: Application No. PCT/IL04/00395.
International Preliminary Report on Patentability dated Aug. 26, 2009 From the International Bureau of WIPO Re.: Application No. PCT/IL2008/000233.
International Preliminary Report on Patentability dated Oct. 29, 2009 From the International Bureau of WIPO Re.: Application No. PCT/IL2008/000509.
International Search Report dated Aug. 5, 2008 From the International Searching Authority Re.: Application No. PCT/IL2008/000309.
International Search Report dated Dec. 6, 2006 From the International Searching Authority Re.: Application No. PCT/IL06/00075.
International Search Report dated Mar. 22, 2005 From the International Searching Authority Re.: Application No. PCT/IL04/00395.
International Search Report dated Mar. 27, 2009 From the International Searching Authority Re.: Application No. PCT/IL2008/001105.
International Search Report dated Jul. 28, 2008 From the International Searching Authority Re.: Application No. PCT/IL2008/000233.
Invitation Pursuant to Rule 62a(1) EPC dated Jun. 10, 2010 From the European Patent Office Re. Application No. 06700959.7.
Notice of Allowability dated Nov. 21, 2012 From the US Patent and Trademark Office Re. U.S. Appl. No. 11/884,227.
Notice of Allowance dated Oct. 25, 2012 From the US Patent and Trademark Office Re. U.S. Appl. No. 11/884,227.
Office Action dated Dec. 12, 2008 From the State Intellectual Property Office of the People's Republic of China Re.: Application No. 200680012560.2.
Office Action dated Apr. 24, 2009 From the State Intellectual Property Office of the People's Republic of China Re.: Application No. 200480019436.X.
Office Action dated Jul. 24, 2009 From the State Intellectual Property Office of the People's Republic of China Re.: Application No. 200680012560.2 and Its Translation Into English.
Official Action dated Aug. 2, 2012 From the US Patent and Trademark Office Re. U.S. Appl. No. 11/884,227.
Official Action dated Nov. 2, 2011 From the US Patent and Trademark Office Re. U.S. Appl. No. 11/884,227.
Official Action dated Oct. 6, 2009 From the US Patent and Trademark Office Re.: U.S. Appl. No. 10/556,483.
Official Action dated Aug. 9, 2012 From the US Patent and Trademark Office Re. U.S. Appl. No. 11/889,395.
Official Action dated Jul. 10, 2012 From the US Patent and Trademark Office Re. U.S. Appl. No. 12/527,697.
Official Action dated Oct. 15, 2012 From the US Patent and Trademark Office Re. U.S. Appl. No. 12/673,037.
Official Action dated Feb. 18, 2009 From the US Patent and Trademark Office Re.: U.S. Appl. No. 10/556,483.
Official Action dated Jun. 22, 2010 From the US Patent and Trademark Office Re.: U.S. Appl. No. 10/556,483.
Official Action dated Oct. 23, 2012 From the US Patent and Trademark Office Re. U.S. Appl. No. 12/450,022.
Official Action dated Jul. 24, 2012 From the US Patent and Trademark Office Re. U.S. Appl. No. 12/596,483.
Official Action dated Aug. 31, 2011 From the US Patent and Trademark Office Re. U.S. Appl. No. 11/884,227.
Patent Examination Report dated Aug. 1, 2012 From the Australian Government, IP Australia Re. Application No. 2008242145.
Patent Examination Report dated Nov. 30, 2012 From the Australian Government, IP Australia Re. Application No. 2008288084.
Requisition by the Examiner dated Jan. 9, 2012 From the Canadian Intellectual Property Office Re. Application No. 2,525,443.
Requisition by the Examiner dated Jul. 24, 2012 From the Canadian Intellectual Property Office Re. Application No. 2,525,443.
Requisition by the Examiner dated May 30, 2012 From the Canadian Intellectual Property Office Re. Application No. 2,597,264.
Response dated Jun. 3, 2010 to Communication Pursuant to Article 94(3) EPC dated Feb. 12, 2010 From the European Patent Office Re.: Application No. 08738211.5.
Response dated Jul. 4, 2010 to Invitation Pursuant to Rule 62a(1) EPC dated Jun. 10, 2010 From the European Patent Office Re. Application No. 06700959.7.
Response dated Apr. 6, 2010 to Official Action dated Oct. 6, 2009 From the US Patent and Trademark Office Re.: U.S. Appl. No. 10/556,483.
Response dated Nov. 8, 2009 to Communication Pursuant to Article 94(3) EPC dated Jul. 8, 2009 From the European Patent Office Re.: Application No. 04731993.4.
Response dated Sep. 11, 2011 to Official Querry dated Jul. 1, 2011 From the Japanese Patent Office Re. Application No. 2006-507622.
Response dated Sep. 12, 2011 to Official Action dated Aug. 31, 2011 From the US Patent and Trademark Office Re. U.S. Appl. No. 11/884,227.
Response dated Nov. 17, 2011 to Examiner's Report dated Nov. 15, 2010 From the Australian Government, IP Australia Re. Application No. 2006215274.
Response dated Jul. 21, 2010 to Notice of Reason for Rejection dated Apr. 6, 2010 From the Japanese Patent Office Re. Application No. 2006-507622.
Response dated Sep. 21, 2010 to Official Action dated Jun. 22, 2010 From the US Patent and Trademark Office Re.: U.S. Appl. No. 10/556,483.
Response dated Jul. 25, 2011 to Communication Pursuant to Article 94(3) EPC dated Jan. 26, 2011 From the European Patent Office Re.: Application No. 04731993.4.
Response dated Jun. 28, 2010 to Communication Pursuant to Article 94(3) EPC dated Dec. 29, 2009 From the European Patent Office Re.: Application No. 08710233.1.
Response dated Dec. 29, 2010 to Notice of Reason for Rejection dated Sep. 17, 2010 From the Japanese Patent Office Re. Application No. 2006-507622.
Response dated Jan. 30, 2011 to Communication Pursuant to Article 94(3) EPC dated Oct. 20, 2010 From the European Patent Office Re. Application No. 08719934.5.
Restriction Official Action dated Jun. 7, 2012 From the US Patent and Trademark Office Re. U.S. Appl. No. 11/889,395.
Supplementary Partial European Search Report dated Apr. 9, 2009 From the European Patent Office Re.: Application No. 04731993.4.
Translation of Notice of Reason for Rejection dated Apr. 6, 2010 From the Japanese Patent Office Re. Application No. 2006-507622.
Translation of Notice of Reason for Rejection dated Sep. 17, 2010 From the Japanese Patent Office Re. Application No. 2006-507622.

(56) References Cited

OTHER PUBLICATIONS

Translation of Official Querry dated Jul. 1, 2011 From the Japanese Patent Office Re. Application No. 2006-507622.
Translation of the Official Action dated Dec. 12, 2008 From the State Intellectual Property Office of the People's Republic of China Re.: Application No. 200680012560.2.
Written Opinion dated Aug. 5, 2008 From the International Searching Authority Re.: Application No. PCT/IL2008/000309.
Written Opinion dated Dec. 6, 2006 From the International Searching Authority Re.: Application No. PCT/IL06/00075.
Written Opinion dated Mar. 22, 2005 From the International Searching Authority Re.: Application No. PCT/Il04/00395.
Written Opinion dated Mar. 27, 2009 From the International Searching Authority Re.: Application No. PCT/IL2008/001105.
Written Opinion dated Jul. 28, 2008 From the International Searching Authority Re.: Application No. PCT/IL2008/000233.
Bakshi et al. "Circulatory Response in Sleep Apnea Patients During Sleep Before and After CPAP Treatment", Sleep, XO008094214, 28(Suppl.S): A194: 0576, 2005. 19th Annual Meeting of the Associated-Professional-Sleep-Societies, Denver, CO, USA, Jun. 18-23, 2005. Abstract.
Delpierre et al. "Doppler Effect With Sound", Electronic Science Tutor, Retrieved From the Internet, 5 P., Oct. 18, 2011.
Ellis "Introduction to Mixers", Retrieved From the Internet, 9 P., 1999.
Goovaerts et al. "A Wideband High Common Mode Rejection Ratio Amplifier for Multifrequency Impedance Measurement", Medical and Biological Engineering and Computing, XP000784850, 36(6): 761-767, Nov. 1, 1998. Section 2.2 'Lock-in Measurement', p. 761, p. 763, col. 2, Figs.2, 3.
Jellinek et al. "Right Atrial Pressure Predicts Hemodynamic Response to Apncic Positive Airway Pressure", Critical Care Medicine, XP002488470, 28(3): 672-678, Mar. 2000. Database Medline [Online], US National Library of Medicine, Database Accession No. NLM10752813. Abstract.
Kubicek et al. "The Minnesota Impedance Cardiograph—Theory and Applications", Biomedical Engineering, XP001051054, 9(9): 410-416, Sep. 1, 1974. p. 411, Middle Col., Figs.1, 2.
Lele et al. "Exercise Capacity in Hypertrophic Cardiomyopathy: Role of Stroke Volume Limitation, Heart. Rate, and Diastolic Filling Characteristics", Circulation, XP002487808, 92(10): 2886-2894, 1995.
Lin et al. "Effects of Hypercapnia, Hypoxia, and Rebreathing on Circulatory Response to Apnea", Journal of Applied Physiology Respiratory Environmental and Exercise Physiology, XP008094195, 54(1): 172-177, 1983.
Miyamoto et al. "Cardiorespiratory Dynamics During Sinusoidal and Impulse Exercise in Man", Japanese Journal of Physiology, XP008094022, 33(6): 971-986, 1983.
Myers et al. "Cardiac Output and Cardiopulmonary Responses to Exercise in Heart Failure: Application of a New Bio-Resistance Device", Journal of Cardiac Failure, XP0022287174, 13(8): 629-636, Oct. 6, 2007.
Newman et al. "The Non-Invasive Assessment of Stroke Volume and Cardiac Output by Impedance Cardiography: A Review", Aviation Space and Environmental Medicine, XP008093991, 70(8): 780-789, Aug. 1999.
Raza et al. "Filtering Respiration and Low-Frequency Movement Artefacts From the Cardiogenic Electrical Impedance Signal", Medical and Biological Engineering and Computing, XP000323425, 30(5): 556-561, Sep. 1, 1992. p. 556, r-h Col., § 3—p. 557, r-h Col., § 1, p. 557, l-h Col., § 3, p. 558, l-h Col., § 2—r-h Col., § 1, Fig.3.
Saarelainen et al. "Whole-Body Impedance Recording—A Practical Method for the Diagnosis of Sleep Apnoea", Clinical Physiology and Functional Imaging, XO002488466, 23(2): 110-113, Mar. 2003.
Schumacker et al. "Oxygen Delivery and Uptake Relationships in Patients With Aortic Stenosis", American Journal of Respiratory and Critical Care Medicine, XP002488468, 149(5): 1123-1131, May 1994. Database Embase [Online], Database Accession No. EMB-1994152503, 1994. Abstract.
Stoohs et al. "Cardiovascular Changes Associated With Obstructive Sleep Apnea Syndrome", Journal of Applied Physiology, XP002488467, 72(2): 583-589, 1992. Database Biosis [Online], Biosciences Information Service, Database Accession No. PREV199293105800, 1992. Abstract.
Tolle et al. "Reduced Stroke Volume Related to Pleural Pressure in Obstructive Sleep Apnea", Journal of Applied Physiology Respiratory Environmental and Exercise Physiology, XP002488469, 55(6): 1718-1724, 1983. Database Biosis [Online], Biosciences Information Service, Database Accession No. PREV198477063246, 1883. Abstract.
Notice of Allowance dated May 10, 2013 From the US Patent and Trademark Office Re. U.S. Appl. No. 12/596,483.
Summons to Attend Oral Proceedings Pursuant to Rule 115(1) EPC Dated Sep. 5, 2013 From the European Patent Office Re. Application No. 04731993.4.
Requisition by the Examiner dated Dec. 6, 2013 From the Canadian Intellectual Property Office Re. Application No. 2,597,264.
Communication Under Rule 71(3) EPC dated Jan. 16, 2014 From the European Patent Office Re. Application No. 04731993.4.
Notice of Allowance dated Mar. 13, 2014 From the US Patent and Trademark Office Re. U.S. Appl. No. 12/450,022.
Official Action dated Mar. 10, 2014 From the US Patent and Trademark Office Re. U.S. Appl. No. 11/889,395.
Notice of Allowance dated Apr. 1, 2014 From the US Patent and Trademark Office Re. U.S. Appl. No. 12/673,037.
Brief Communication for Oral Proceedings on Dec. 10, 2013 Dated Dec. 3, 2013 From the European Patent Office Re. Application No. 04731993.4.
Scofield "A Frequency-Domain Description of a Lock-in-Amplifier", American Journal of Physics, XP009097728, 62(2): 129-133, Feb. 1, 1994.
Corrected Notice of Allowability dated Aug. 13, 2014 From the US Patent and Trademark Office Re. U.S. Appl. No. 12/527,697.
Supplementary Partial European Search Report dated Jul. 2, 2014 From the European Patent Office Re. Application No. 06700959.7.
Requisition by the Examiner dated Dec. 2, 2014 From the Canadian Intellectual Property Office Re. Application No. 2,597,264.
Official Action dated Dec. 8, 2014 From the US Patent and Trademark Office Re. U.S. Appl. No. 11/889,395.
Requisition by the Examiner and Examination Search Report dated Dec. 15, 2014 From the Canadian Intellectual Property Office Re. Application No. 2,695,726.
Notice of Allowance dated Mar. 25, 2015 From the US Patent and Trademark Office Re. U.S. Appl. No. 11/889,395.
Requisition by the Examiner and Examination Search Report dated Feb. 4, 2015 From the Canadian Intellectual Property Office Re. Application No. 2,683,684.
Requisition by the Examiner dated May 3, 2016 From the Canadian Intellectual Property Office Re. Application No. 2,597,264.
Requisition by the Examiner dated Dec. 1, 2015 From the Canadian Intellectual Property Office Re. Application No. 2,695,726.
Requisition by the Examiner dated Nov. 18, 2015 From the Canadian Intellectual Property Office Re. Application No. 2,597,264.
Restriction Official Action dated Dec. 27, 2016 From the US Patent and Trademark Office Re. U.S. Appl. No. 14/738,982. (6 pages).
Examination Report Under Sections 12 & 13 of the Patents Act, 1970 and the Patents Rules, 2003 dated Dec. 5, 2017 From the Government of India, Intellectual Property India, Patents, Designs, Trade Marks, Geographical Indications Re. Application No. 6787/CHENP/2009. (6 Pages).
Tchoudovski et al. "New Approach in Developing of the Algorithms for Resuscitation Assistance", Proceedings of the 26th Annual International Conference of the IEEE Engineering in Medicine and Biology Society, San Francisco, CA, USA, Sep. 1-5, 2004, 2: 956-959, Sep. 1, 2004.
Official Action dated Feb. 8, 2018 From the US Patent and Trademark Office Re. U.S. Appl. No. 14/738,982. (23 pages).
Official Action dated Jun. 30, 2017 From the US Patent and Trademark Office Re. U.S. Appl. No. 14/738,982. (50 pages).
Examination Report Under Sections 12 & 13 of the Patents Act, 1970 and the Patents Rules, 2003 dated Aug. 24, 2017 From the

(56) References Cited

OTHER PUBLICATIONS

Government of India, Intellectual Property India, Patents, Designs, Trade Marks, Graphical Indications Re. Application No. 473/MUMNP/2010. (7 Pages).
Official Action dated Sep. 6, 2019 From the US Patent and Trademark Office Re. U.S. Appl. No. 141738,982. (11 pages).
Official Action dated Mar. 8, 2019 From the US Patent and Trademark Office Re. U.S. Appl. No. 14/738,982. (15 pages).
Hearing Notice dated Jan. 27, 2020 From the Government of India, Intellectual Property India, Patent Office, Intellectual Property Building Re. Application No. 473/MUMNP/2010. (3 pages).

* cited by examiner

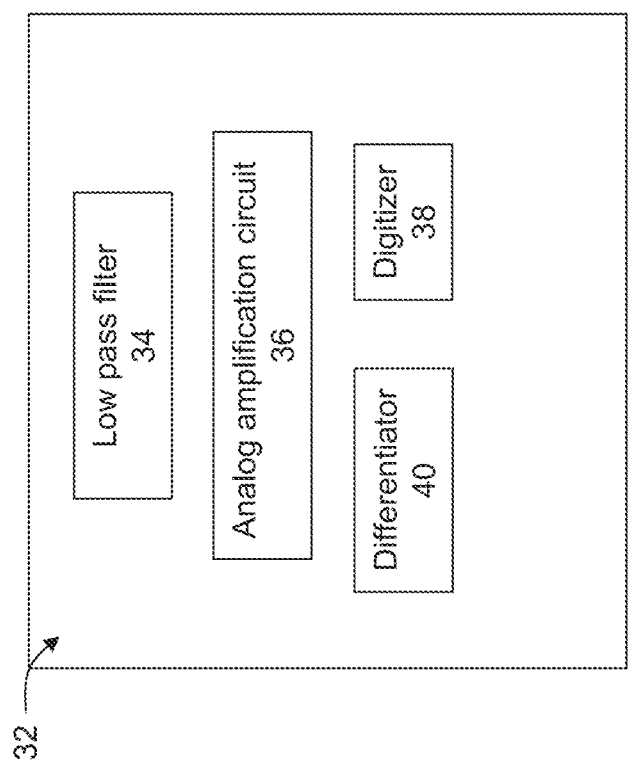

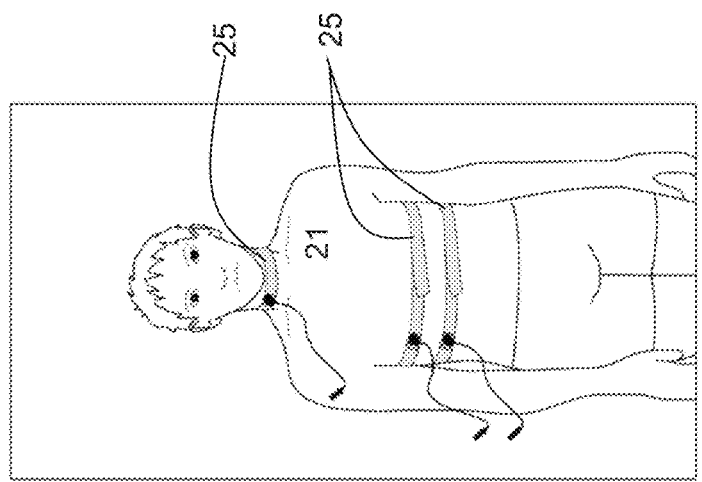
Fig. 4a
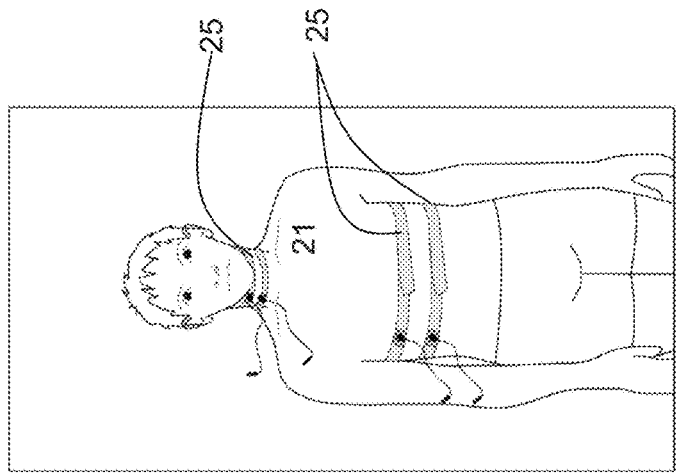
Fig. 4b
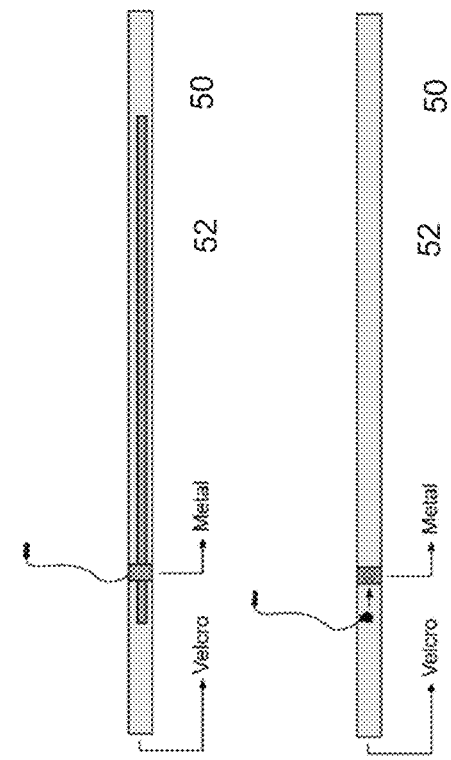
Fig. 4c
Fig. 4d

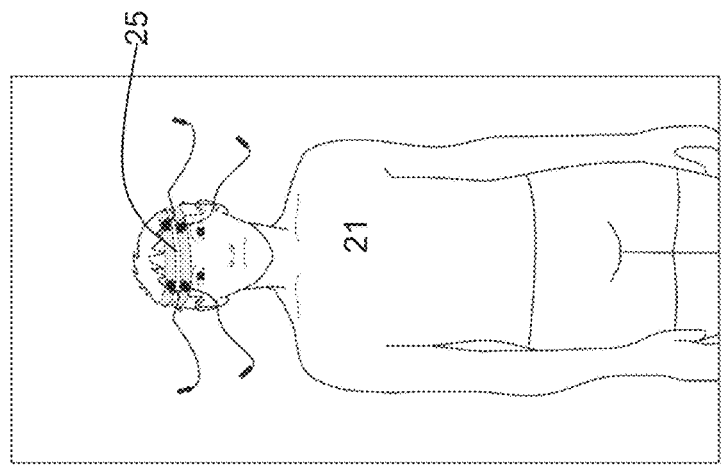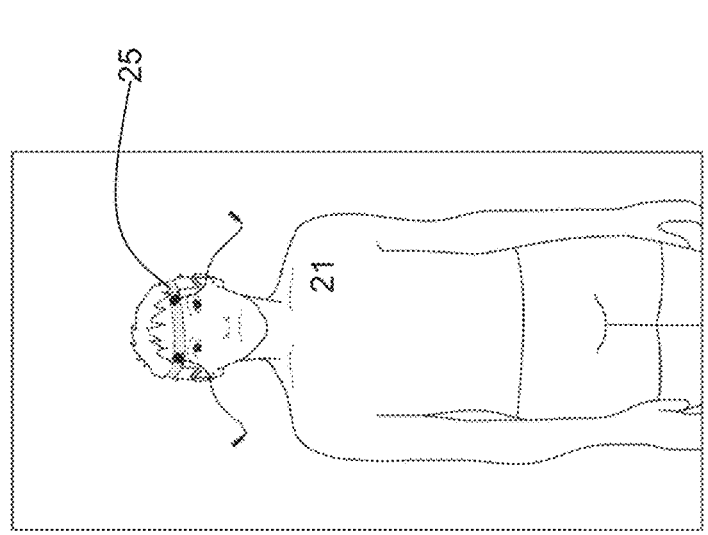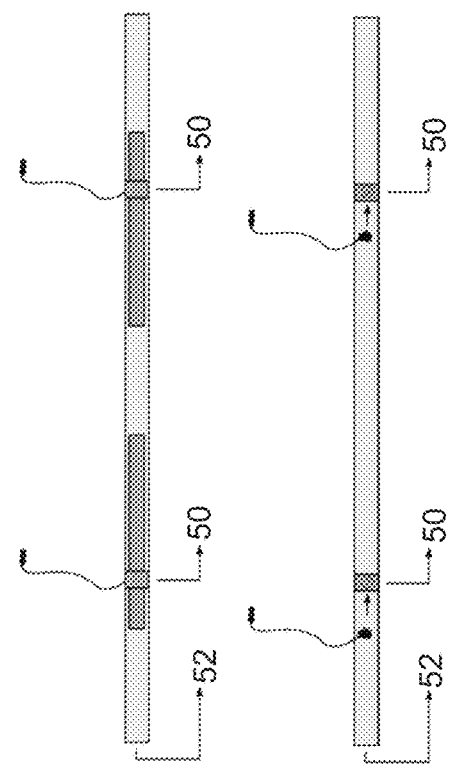

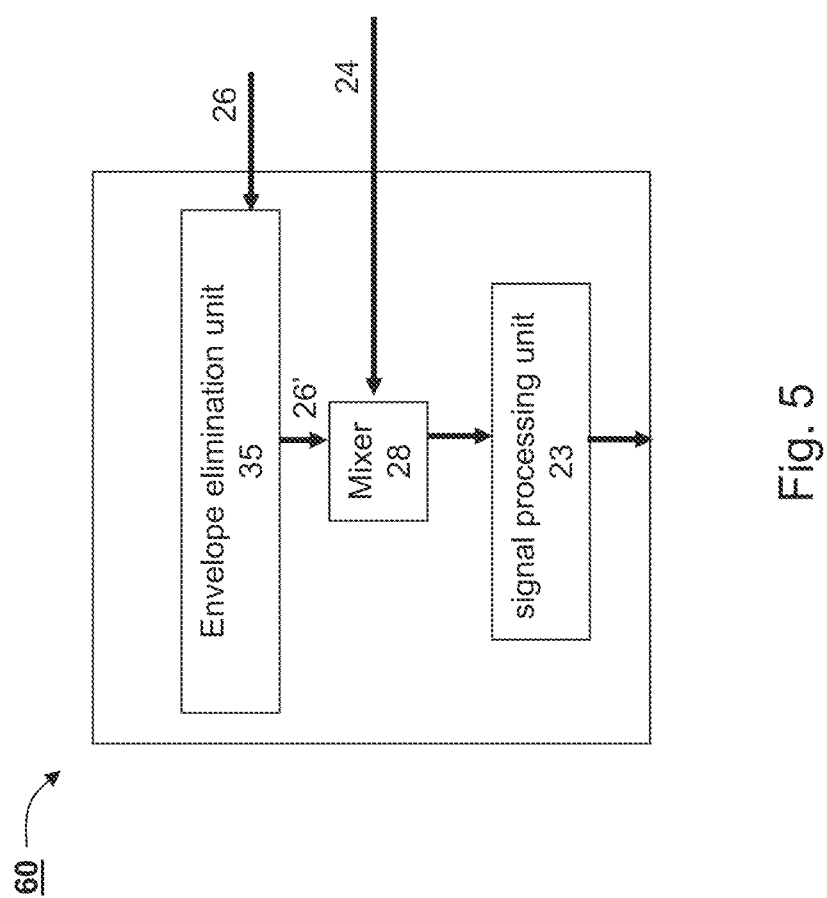

SYSTEM, METHOD AND APPARATUS FOR MEASURING BLOOD FLOW AND BLOOD VOLUME

RELATED APPLICATIONS

This application is a divisional of U.S. patent application Ser. No. 11/884,227 filed on Aug. 13, 2007, which is a National Phase of PCT Patent Application No. PCT/IL2006/000075 having International Filing Date of Jan. 18, 2006, which claims the benefit of priority of U.S. Provisional Patent Application No. 60/652,773 filed on Feb. 15, 2005. The contents of the above applications are all incorporated herein by reference.

FIELD AND BACKGROUND OF THE INVENTION

The present invention relates to measurement of electrical signals of a body of a subject and, more particularly, to measurement of electrical signals of the body of the subject so as to determine blood volume or blood volume rate, e.g., stroke volume, cardiac output, brain intra luminal blood volume and the like.

Heart diseases are major causes of morbidity and mortality in the modern world. Generally, heart diseases may be caused by (i) a failure in the autonomic nerve system where the impulses from the central nervous system control to the heart muscle fail to provide a regular heart rate and/or (ii) an insufficient strength of the heart muscle itself where even though the patient has a regular heart rate, its force of contraction is insufficient. Either way, the amount of blood or the rate at which the blood is supplied by a diseased heart is abnormal and it is appreciated that an assessment of the state of a patient's circulation is of utmost importance.

The simplest measurements, such as heart rate and blood pressure, may be adequate for many patients, but if there is a cardiovascular abnormality then more detailed measurements are needed.

Cardiac output (CO) is the volume of blood pumped by the heart during a time interval, which is typically taken to be a minute. Cardiac output is the product of heart rate (HR) and the amount of blood which is pumped with each heartbeat, also known as the stroke volume (SV). For example, the stroke volume at rest in the standing position averages between 60 and 80 ml of blood in most adults. Thus, at a resting heart rate of 80 beats per minute the resting cardiac output varies between 4.8 and 6.4 L per min.

A common clinical problem is that of hypotension (low blood pressure); this may occur because the cardiac output is low and/or because of low systemic vascular resistance. This problem can occur in a wide range of patients, especially those in intensive care or postoperative high dependency units. In these high risk patients, more detailed monitoring is typically established including measuring central venous pressure via a central venous catheter and continuous display of arterial blood pressure via a peripheral arterial catheter.

In addition to the above measurements, the measurement of cardiac output is extremely important. For example, when combined with arterial pressure measurements, cardiac output can be used for calculating the systemic vascular resistance. The measurement of cardiac output is useful both for establishing a patient's initial cardiovascular state and for monitoring the response to various therapeutic interventions such as transfusion, infusion of inotropic drugs, infusion of vasoactive drugs (to increase or reduce systemic vascular resistance) or altering heart rate either pharmacologically or by adjusting pacing rate.

Several methods of measuring cardiac output are presently known. One such method is known as the Fick method, described by Adolf Fick in 1870. This method is based on the observation that the amount of oxygen picked up by the blood as it passes through the lungs is equal to the amount of oxygen taken up by the lungs during breathing. In Fick's method, one measures the amount of oxygen taken up by the body during respiration and the difference in oxygen concentration between venous and arterial blood and uses these measurements to calculate the amount of blood pumped through the lungs which is equal to the cardiac output. More specifically, in Fick's method the cardiac output equals the ratio between the oxygen consumption and the arteriovenous oxygen content difference.

Oxygen consumption is typically measured non-invasively at the mouth, while the blood concentrations are measured from mixed venous and peripheral arterial blood drawings. Oxygen consumption is derived by measuring the volume of an expired gas over a certain period of time and the difference in oxygen concentration between the expired gas and the inspired gas.

The Fick method suffers from many drawbacks. First, accurate collection of the gas is difficult unless the patient has an endotracheal tube because of leaks around a facemask or mouthpiece. Second, the analysis of the gas, which is straightforward if the inspired gas is air, is problematic for oxygen enriched air. Third, the arteriovenous oxygen content difference presents a further problem in that the mixed venous (i.e., pulmonary arterial) oxygen content has to be measured and therefore a pulmonary artery catheter is needed to obtain the sample, which may cause complications to the patient.

The Fick principle can also be applied with $CO_2$ instead of oxygen, by measuring $CO_2$ elimination which can be determined more easily as compared to oxygen consumption. With this variant of Fick's method, cardiac output is proportional to the change in $CO_2$ elimination divided by the change in end tidal $CO_2$ resulting from a brief rebreathing period. These changes are accomplished and measured by a sensor, which periodically adds a rebreathing volume into the breathing circuit. Although this method improves the ability to perform accurate measurements of gas, it still suffers from most of the above limitations, in particular the limitation related to leaks around the facemask.

Another method is by transoesophageal echocardiography (TOE) which provides diagnosis and monitoring of a variety of structural and functional abnormalities of the heart. TOE is used to derive cardiac output from measurement of blood flow velocity by recording the Doppler shift of ultrasound reflected from the red blood cells. The time velocity integral, which is the integral of instantaneous blood flow velocities during one cardiac cycle, is obtained for the blood flow in a specific site (e.g., the left ventricular outflow tract). The time velocity integral is multiplied by the cross-sectional area and the heart rate to give cardiac output. Besides being very inaccurate, the method has the following disadvantages: (i) the system may only be operated by a skilled operator; (ii) due to the size of the system's probe, heavy sedation or anesthesia is needed; (iii) the system is expensive; and (iv) the probe cannot be configured to provide continuous cardiac output readings without an expert operator being present.

U.S. Pat. No. 6,485,431 discloses a relatively simple method in which the arterial pressure, measured by a pressure cuff or a pressure tonometer, is used for calculating the mean arterial pressure and the time constant of the arterial system in diastole. The compliance of the arterial system is then determined from a table and used for calculating the cardiac output as the product of the mean arterial pressure and compliance divided by a time constant. This method, however, is very inaccurate and it can only provide a rough estimation of the cardiac output.

An additional method of measuring cardiac output is called thermodilution. This method is based on a principle in which the cardiac output can be estimated from the dilution of a bolus of saline being at a different temperature from the blood. The thermodilution involves an insertion of a fine catheter into a vein, through the heart and into the pulmonary artery. A thermistor, mounted on the tip of the catheter senses the temperature in the pulmonary artery. A bolus of saline (about 5 ml. in volume) is injected rapidly through an opening in the catheter, located in or near to the right atrium of the heart. The saline mixes with the blood in the heart and temporarily depresses the temperature in the right atrium. Two temperatures are measured simultaneously: the blood temperature is measured by the thermistor sensor on the catheter and the temperature of the saline to be injected is typically measured by means of a platinum temperature sensor. The cardiac output is inversely related to the area under the curve of temperature depression.

The placement of the catheter into the pulmonary artery is expensive and has associated risk including: death; infection; hemorrhage; arrhythmias; carotid artery; thoracic duct, vena caval, tracheal, right atrial, right ventricular, mitral and tricuspid valvular and pulmonary artery injury. Little evidence suggests that placement of a pulmonary artery catheter improves survival and several suggest an increase in morbidity and mortality.

A non-invasive method, known as thoracic electrical bioimpedance, was first disclosed in U.S. Pat. No. 3,340,867 and has recently begun to attract medical and industrial attention [U.S. Pat. Nos. 3,340,867, 4,450,527, 4,852,580, 4,870,578, 4,953,556, 5,178,154, 5,309,917, 5,316,004, 5,505,209, 5,529,072, 5,503,157, 5,469,859, 5,423,326, 5,685,316, 6,485,431, 6,496,732 and 6,511,438; U.S. Patent Application No. 200201936891. The thoracic electrical bioimpedance method has the advantages of providing continuous cardiac output measurement at no risk to the patient.

A typical bioimpedance system includes a tetrapolar array of circumferential band electrodes connected to the subject at the base of the neck and surrounding the circumference of the lower chest, at the level of the xiphoid process. When a constant magnitude alternating current flows through the upper cervical and lower thoracic band electrodes, a voltage, proportional to the thoracic electrical impedance (or reciprocally proportional to the admittance), is measured between the inner cervical and thoracic band electrodes. The portion of the cardiac synchronous impedance change, temporally concordant with the stroke volume, is ascribed solely and uniquely to volume changes of the aorta during expansion and contraction over the heart cycle.

A major disadvantage of existing bioimpedance systems is that the bioimpedance detectors utilized in such systems require several consecutive levels of amplifier circuits. Each amplifier circuit undesirably amplifies the input noise from signals detected in a body segment, thereby necessitating an increase in the magnitude of the measurement current to maintain a reasonable signal-to-noise ratio. Multiple amplifier circuits require substantial area on printed circuit boards and utilize numerous circuit components thereby increasing the cost and power consumption of the system. The complexity of multiple amplifier systems decreases the reliability of the systems and increases the frequency of required maintenance.

A typical printed circuit board of a bioimpedance system comprises one or more band pass filters, a half-wave rectification circuit and one or more low pass filters. One skilled in the art would appreciate that the noise level is proportional to the bandwidth of the band pass filter. As presently available band pass filters are typically characterized by a frequency ratio of about 5%, a considerable portion of the noise passes the band pass filter hence being folded into the half-wave rectification circuit. This problem is aggravated by the fact that the typical change in the impedance within the thorax is about 0.1%, thereby causing a rather low signal-to-noise ratio for such systems.

A recognized problem in bioimpedance measurement is the difficulty in separating and differentiating between cardiovascular bioimpedance signals and respiratory bioimpedance signals, where the latter are typically much larger than the former. An optimization method for increasing the efficiency of the bioimpedance measurement is disclosed in U.S. Pat. No. 4,870,578. In this method, changes in the electrical resistance caused by respiration are suppressed by a clamping circuit, synchronized with the electrical activity of the heart. The clamping circuit is timed to clamp the voltages in the measuring equipment to a baseline reference voltage in the time preceding the beginning of mechanical systole. The voltage clamping is released during the mechanical systole of the heart so that the changes in the bioimpedance caused by the pumping action of the heart during mechanical systole are measured. Although providing a certain degree of improvement to the efficiency of the measurement, this method still suffers from a rather low signal-to-noise ratio.

Additionally, prior art techniques suffer from the limitation of a substantially high level of AM noise which significantly reduces the ability to provide accurate measurement.

There is thus a widely recognized need for and it would be highly advantageous to have, a system, method and apparatus for measuring blood flow devoid of the above limitations.

SUMMARY OF THE INVENTION

According to one aspect of the present invention there is provided a method of calculating blood flow in an organ of a subject using output radiofrequency signals transmitted to the organ and input radiofrequency signals received from the organ, the method comprises determining a phase shift of the input radiofrequency signals relative to the output radiofrequency signals and using the phase shift to calculate the blood flow in the organ.

According to further features in preferred embodiments of the invention described below, the use of the phase shift for calculating the blood flow comprises using a linear relationship between the phase shift and the blood flow.

According to another aspect of the present invention there is provided an apparatus for calculating blood flow in an organ of a subject from output radiofrequency signals transmitted to the organ and input radiofrequency signals received from the organ, the apparatus comprises a signal processing unit for determining a phase shift of the input radiofrequency signals relative to the output radiofrequency signals, and a blood flow calculator for calculating the blood flow in the organ using the phase shift.

According to further features in preferred embodiments of the invention described below, the blood flow calculator is operable to calculate the blood flow using a linear relationship between the phase shift and the blood flow.

According to yet another aspect of the present invention there is provided a system for measuring blood flow in an organ of a subject, the system comprises: a radiofrequency generator for generating output radiofrequency signals; a plurality of electrodes, designed to be connectable to the skin of the subject, the electrodes being for transmitting the output radiofrequency signals to the organ and for sensing input radiofrequency signals of the organ; and a signal processing unit for determining a phase shift of the input radiofrequency signals relative to the output radiofrequency signals, the phase shift being indicative of the blood flow in the organ.

According to further features in preferred embodiments of the invention described below, the signal processing unit comprises an envelope elimination unit designed and configured to reduce or eliminate amplitude modulation of the input radiofrequency signals so as to provide input radiofrequency signals of substantially constant envelope.

According to still further features in the described preferred embodiments the signal processing unit comprises: a mixer, electrically communicating with the radiofrequency generator and at least a portion of the plurality of electrodes, the mixer being designed and configured to mix the output radiofrequency signals and the input radiofrequency signals, to provide a mixed radiofrequency signal being indicative of the blood flow; and electronic circuitry for filtering out a portion of the mixed radiofrequency signal so as to substantially increase a signal-to-noise ratio of a remaining portion of the mixed radiofrequency signal.

According to still further features in the described preferred embodiments the system further comprises a data processor for calculating at least one quantity using the remaining portion of the mixed radiofrequency signal, the at least one quantity being selected from the group consisting of a stroke volume, a cardiac output, a brain intra luminal blood flow and an artery blood flow rate.

According to still further features in the described preferred embodiments the system further comprises a pacemaker, communicating with the data processor and operable to control a heart rate of the subject, wherein the data processor is programmed to electronically control the pacemaker, in accordance with a value of the at least one quantity.

According to still further features in the described preferred embodiments the system further comprises a drug administrating device, communicating with the data processor and operable to administrate drugs to the subject, wherein the data processor is programmed to electronically control the drug administrating device, in accordance with a value of the at least one quantity.

According to still further features in the described preferred embodiments the system further comprises a cardiac assist device, communicating with the data processor and operable to increase the cardiac output.

According to still further features in the described preferred embodiments the cardiac assist device comprises a reinforcing member designed and configured to restrict an expansion of a portion of a heart tissue, thereby to increase the cardiac output.

According to still further features in the described preferred embodiments at least a portion of the plurality of electrodes are designed and constructed to so as to have a substantial constant sensitivity to electrical signals transmitted through the electrodes, irrespectively of an orientation of the electrodes on the subject.

According to still further features in the described preferred embodiments at least a portion of the plurality of electrodes comprises an attaching material.

According to still further features in the described preferred embodiments the system further comprises a detector electrically communicating with at least a portion of the plurality of electrodes for detecting a voltage between a first location and a second location of the subject and for generating the input radiofrequency signals in response to the voltage, wherein the input radiofrequency signals being indicative of impedance and/or hemodynamic reactance of the organ.

According to still further features in the described preferred embodiments the system further comprises at least one sensor for sensing the voltage, the at least one sensor being designed and constructed for generating signals having a magnitude which is a function of blood flow in, from or to the organ.

According to still further features in the described preferred embodiments the electronic circuitry comprises a differentiator for performing at least one time-differentiation, to provide a respective derivative of the impedance and/or hemodynamic reactance of the organ.

According to still further features in the described preferred embodiments the differentiator is selected from the group consisting of a digital differentiator and an analog differentiator.

According to still further features in the described preferred embodiments the system further comprises a display device for displaying the blood flow.

According to still another aspect of the present invention there is provided a method of measuring blood flow in an organ of a subject, the method comprises: generating output radiofrequency signals; transmitting the output radiofrequency signals to the organ and sensing input radiofrequency signals of the organ; and determining a phase shift of the input radiofrequency signals relative to the output radiofrequency signals and using the phase shift to calculate the blood flow in the organ.

According to further features in preferred embodiments of the invention described below, the use of the phase shift for calculating the blood flow comprises using a linear relationship between the phase shift and the blood flow.

According to still further features in the described preferred embodiments the method further comprises reducing or eliminating amplitude modulation of the input radiofrequency signals, so as to provide input radiofrequency signals of substantially constant envelope.

According to still further features in the described preferred embodiments the reducing or eliminating the amplitude modulation comprises maintaining a phase modulation of the input radiofrequency signals of substantially constant envelope.

According to still further features in the described preferred embodiments the method further comprises mixing the output radiofrequency signals and the input radiofrequency signals so as to provide a mixed radiofrequency signal being indicative of the blood flow, and filtering out a portion of the mixed radiofrequency signal so as to substantially increase a signal-to-noise ratio of a remaining portion of the mixed radiofrequency signal.

According to still further features in the described preferred embodiments the mixing comprises providing a radiofrequency sum and a radiofrequency difference.

According to still further features in the described preferred embodiments the filtering the portion of the mixed radiofrequency signal is by a low pass filter designed and constructed for filtering out the radiofrequency sum.

According to still further features in the described preferred embodiments the method further comprises analogically amplifying the remaining portion of the mixed radiofrequency signal.

According to still further features in the described preferred embodiments the method further comprises digitizing the remaining portion of the mixed radiofrequency signal.

According to still further features in the described preferred embodiments the method further comprises calculating at least one quantity using the remaining portion of the mixed radiofrequency signal, the at least one quantity being selected from the group consisting of a stroke volume, a cardiac output and a brain intra luminal blood volume and an artery blood flow rate.

According to still further features in the described preferred embodiments the artery blood flow rate is selected from the group consisting of an external carotid blood flow rate, an internal carotid blood flow rate, an ulnar blood flow rate, a radial blood flow rate, a brachial blood flow rate, a common iliac blood flow rate, an external iliac blood flow rate, a posterior tibial blood flow rate, an anterior tibial blood flow rate, a peroneal blood flow rate, a lateral plantar blood flow rate, a medial plantar blood flow rate, a deep plantar blood flow rate.

According to still further features in the described preferred embodiments the method further comprises controlling a heart rate of the subject in accordance with a value of the at least one quantity.

According to still further features in the described preferred embodiments the controlling a heart rate of the subject is by a pacemaker.

According to still further features in the described preferred embodiments the method further comprises using a value of the at least one quantity for selecting an amount and a type of drugs and administrating the amount and the type of drugs to the subject.

According to still further features in the described preferred embodiments the method further comprises providing a site of surgical access to a portion of a heart of a subject and maintaining the reduction of cardiac expansion of the portion of the heart a substantial amount of time so as to increase the cardiac output.

According to still further features in the described preferred embodiments the transmitting the output radiofrequency signals to the organ and sensing the input radiofrequency signals of the organ is by connecting a plurality of electrodes to the skin of the subject.

According to still further features in the described preferred embodiments a number of the plurality of electrodes is selected so as to substantially decouple the input radiofrequency signals from at least one effect selected from the group consisting of a posture changes effect, a respiration effect and a motion effect.

According to still further features in the described preferred embodiments the plurality of electrodes comprises two electrodes.

According to still further features in the described preferred embodiments the plurality of electrodes comprises three electrodes.

According to still further features in the described preferred embodiments the plurality of electrodes comprises four electrodes.

According to still further features in the described preferred embodiments the connecting the plurality of electrodes is done so as to have a substantial constant sensitivity to electrical signals transmitted through the electrodes, irrespectively of an orientation of the electrodes on the subject.

According to still further features in the described preferred embodiments at least a portion of the plurality of electrodes comprises at least one elongated conducting material designed and constructed to wind at least a portion of an external organ of the subject, so as to have a substantial constant sensitivity to electrical signals transmitted through the electrodes, irrespectively of an orientation of the electrodes on the external organ.

According to still further features in the described preferred embodiments the external organ is selected from the group consisting of a chest, a hip, a thigh, a neck, a head, an arm, a forearm, an abdomen, a gluteus, a leg and a foot.

According to still further features in the described preferred embodiments the method further comprises detecting a voltage between a first location and a second location of the subject and generating the input radiofrequency signals in response to the voltage, wherein the input radiofrequency signals being indicative of impedance and/or hemodynamic reactance of the organ.

According to still further features in the described preferred embodiments the method further comprises performing at least one time-differentiation thereby providing a respective derivative of the impedance and/or hemodynamic reactance of the organ.

According to still further features in the described preferred embodiments the derivative is selected from the group consisting of a first derivative and a second derivative.

According to still further features in the described preferred embodiments the performing the time-differentiation is effected by a procedure selected from the group consisting of a digital differentiation and an analog differentiation.

According to still further features in the described preferred embodiments the method further comprises displaying the blood flow using a display device.

According to still further features in the described preferred embodiments the display device is capable of displaying the blood flow as a function of time.

According to an additional aspect of the present invention there is provided an apparatus for determining blood flow in an organ of a subject from output radiofrequency signals transmitted to the organ and input radiofrequency signals received from the organ, the apparatus comprises: electronic circuitry having an envelope elimination unit designed and configured to reduce or eliminate amplitude modulation of the input radiofrequency signals thereby to provide input radiofrequency signals of substantially constant envelope; and a signal processing unit for determining the blood flow in the organ using the input radiofrequency signals of substantially constant envelope.

According to further features in preferred embodiments of the invention described below, the signal processing unit is designed and configured to determine a phase shift of the input radiofrequency signals relative to the output radiofrequency signals of substantially constant envelope, the phase shift being indicative of the blood flow in the organ.

According to still further features in the described preferred embodiments the envelope elimination unit is designed and configured to maintain a phase modulation of the input radiofrequency signals.

According to still further features in the described preferred embodiments the envelope elimination unit comprises a limiter amplifier.

According to still further features in the described preferred embodiments the apparatus further comprises a mixer, for mixing the output radiofrequency signals and the input radiofrequency signals of substantially constant envelope thereby to provide a mixed radiofrequency signal.

According to still further features in the described preferred embodiments the electronic circuitry is designed and configured to filter out a portion of the mixed radiofrequency signal so as to substantially increase a signal-to-noise ratio of a remaining portion of the mixed radiofrequency signal.

According to still further features in the described preferred embodiments the mixer is operable to provide a radiofrequency sum and a radiofrequency difference.

According to still further features in the described preferred embodiments the electronic circuitry comprises a low pass filter for filtering out the radiofrequency sum.

According to still further features in the described preferred embodiments the electronic circuitry comprises an analog amplification circuit for amplifying the remaining portion of the mixed radiofrequency signal.

According to still further features in the described preferred embodiments the electronic circuitry comprises a digitizer for digitizing the remaining portion of the mixed radiofrequency signal. According to still further features in the described preferred embodiments the electronic circuitry is designed and constructed so as to minimize sensitivity of the input radiofrequency signals to impedance differences between the plurality of electrodes and the organ of the subject.

According to still further features in the described preferred embodiments the electronic circuitry comprises at least one differential amplifier characterized by an impedance being substantially larger than the impedance differences between the plurality of electrodes and the organ of the subject.

According to still further features in the described preferred embodiments the signal-to-noise ratio is increased by at least 10 dB, more preferably by at least 20 dB, most preferably by at least 30 dB.

The present invention successfully addresses the shortcomings of the presently known configurations by providing a system, method and apparatus for measuring and/or calculating blood flow, far exceeding prior art technologies.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3 is a schematic illustration of electronic circuitry for filtering out a portion of a signal so that a remaining portion of the signal is characterized by a substantially increased signal-to-noise ratio;

FIGS. 4*a-h* are schematic illustrations of electrodes (c, d, g and h) and the respective positions to which the electrodes are attached (a, b, e and f), according to a preferred embodiment of the present invention;

FIG. 5 is a schematic illustration of an apparatus for determining blood flow in an organ of a subject, according to a preferred embodiment of the present invention;

DESCRIPTION OF THE PREFERRED EMBODIMENTS

The present invention is of a system, method and apparatus for measuring blood flow in an organ of a subject, which can be used for determining many blood-flow related parameters for the purpose of medical diagnosis and/or treatment. Specifically, the present invention can be used for determining stroke volume, cardiac output, brain intra luminal blood volume and blood flow in other arteries of the body such as, but not limited to, arteries in the chest, hip, thigh, neck, head, arm, forearm, abdomen, gluteus, leg and foot.

Figure 1:
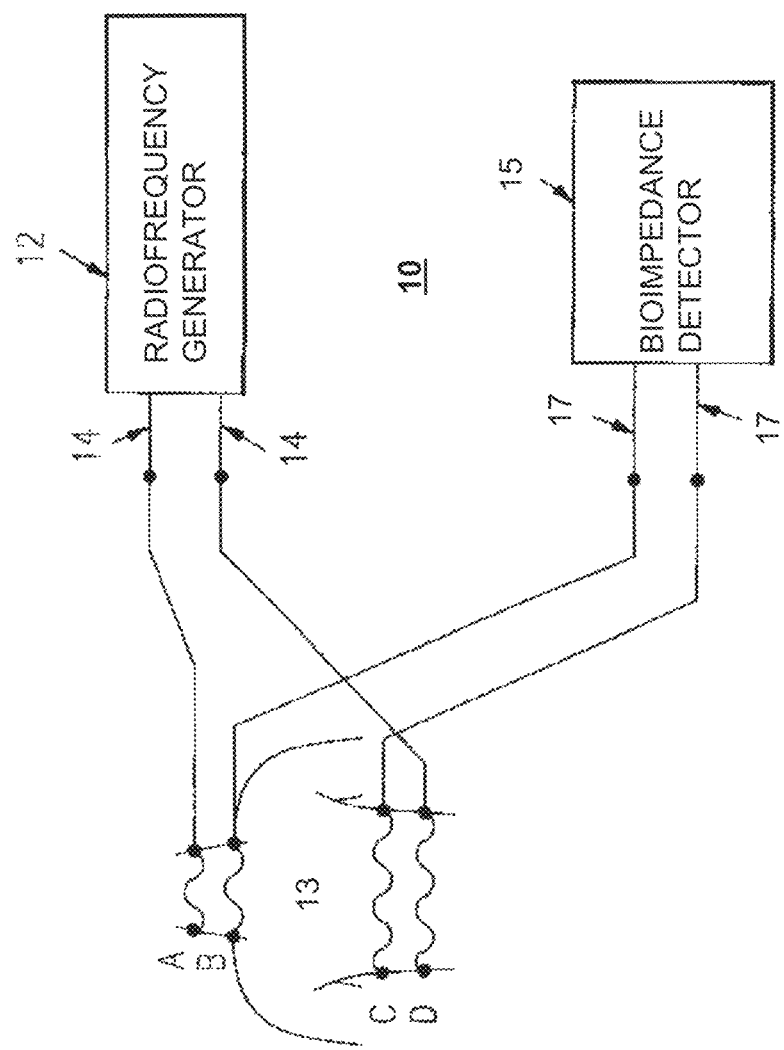
FIG. 1 is a schematic illustration of a conventional bioimpedance system, according to prior art teachings.

For purposes of better understanding the present invention, as illustrated in FIGS. 2-9b of the drawings, reference is first made to the construction and operation of a conventional (i.e., prior art) system for determining blood flow as illustrated in FIG. 1.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates the conventional system, generally referred to herein as system 10, which includes a radiofrequency generator 12 for generating a periodic high frequency current output in response to a periodic control input signal. System 10 further includes output spot electrodes 14 for carrying current output from radiofrequency generator 12. Electrodes 14 are connected to locations of a human body 13 above and below the heart. Shown in FIG. 1 are two output spot electrodes, connected to two pairs of locations, a first pair A and a second pair D, hence form a tetrapolar array of electrodes. Current, generated by radiofrequency generator 12, flows between location pairs A and D and causes a voltage drop on the segment A-D, due to the impedance of body 13.

System 10 further includes an electrical bioimpedance detector 15 and four additional electrodes for detecting a voltage signal, between two additional location pairs designated B and C, located respectively in proximity to pairs A and D and, similarly to electrodes 14, form a tetrapolar array of electrodes. Bioimpedance detector 15 is connected to body 13 through two input spot electrodes 17. Detector 15 generates an output signal indicative of the impedance of segment B-C, in response to the voltage signal received by electrodes 17.

The voltage signal is proportional to the magnitude of the periodic current and also proportional to the electrical bioimpedance of the tissue between the pairs A and D (or pairs B and C).

The radiofrequency generator typically generates a high frequency current a few milliamperes Root Mean Square in magnitude and a few tens of kilohertz in frequency.

The amplitude of the voltage signal is modulated by changes in conductivity in the body segment. In the thorax, such changes are due to changes in the volume of blood within the thorax and by orientation of erythrocytes as a function of blood flow velocity in major arteries. The voltage signal modulation envelope is a superimposed sum of conductivity changes caused by changes in posture, respiration, cardiac cycle, motion artifacts and electrical noise.

The determination of the blood flow is thus by measuring the impedance change, $\Delta Z$ and calculating the blood flow therefrom. The ability of system 10 and similar prior art systems to measure blood flow depends on several assumptions which model the dependence of the blood flow on the impedance, Z. More specifically, it is assumed that the change in thoracic impedance is due to the pulsatile nature of blood flow and that effect of ventilation (changes in chest size) can be neglected.

It is further assumed is that all impedance changes are due to the variation of aortic blood volume, while pulmonary circulation are neglected and venous return are considered as constant. Thus, the total impedance Z is typically approximated to $Z=\rho L/A$, where $\rho$ is the resistivity of the blood, L is the distance between the electrodes and A is its cross-sectional area. Assuming that the aorta has a cylindrical shape and that the changes in the blood resistivity are small, the time dependence of the aortic volume V can be written as $V(t)=\rho L^2/Z(t)$, where $Z(t)=\rho L/A(t)$. It is recognized, however, that a non-invasive measurement of the explicit time-dependence of $Z(t)$ is not achievable and one can only measure a static thoracic impedance, $Z_0$.

Under the assumptions that (i) the resistivity of the blood is similar to the resistivity of the thoracic tissues, and (ii) the thorax has a cylindrical shape with a single chamber in parallel with the aorta, $Z_0$ satisfies, $1/Z_0=1/Z_c+1/Z_a$, where $Z_c$ and $Z_a$ are the impedances of the thorax and the aorta, respectively. Assuming further that $|Z_0-Z_c|<1\%$, the pulsatile change in the aortic volume $\Delta V$ change is volume can be approximated to $\Delta V=\rho L^2/Z_0^2 \Delta Z$. As the relation between $\Delta V$ and the stroke volume, SV depends on the net flux of blood (SV=$V_0$+input flow−output flow), additional modeling have to be made in order to extrapolate SV. These models can include independent assessment of aortic valve closure or the substitution of the maximal time-derivative of the aortic impedance, $(dZ/dt)_{max}$ and the systolic ejection time, T, into the derivative of $\Delta V$: $SV=d(\Delta V)/dt=\rho L^2/Z_0^2 T (dZ/dt)_{max}$.

The time-derivative of the impedance is proportional to the impedance change, $\Delta Z$. Typically, however, the value of the impedance change, $\Delta Z$, is smaller than the value of the impedance, Z, by 2-4 orders of magnitude, thus affecting the quality of the measurement in terms of signal-to-noise ratio. The noise content of the received signal can be reduced by the use of one or more band pass filters, filtering out frequencies below a low threshold and above a high threshold. Nevertheless, the efficiency of known band pass filters is insufficient and the resulting signal still has a substantial amount of the noise content folded therein.

Additionally, the above formula for calculating SV includes many measurement-dependent coefficients which contribute to the aggregated error of the total measurement. Specifically, errors in the measurements of the static impedance $Z_0$, the distance between the electrodes L and/or the systolic ejection time T, significantly increase the uncertainty in the stroke volume.

Still additionally, impedance measurement as performed by system 10 and other prior art systems suffer from considerable AM noise which further increases the uncertainty in the stroke volume.

The present embodiments successfully overcome the above shortcomings by providing system for measuring blood flow in an organ of a subject, generally referred to herein as system 20.

Figure 2:
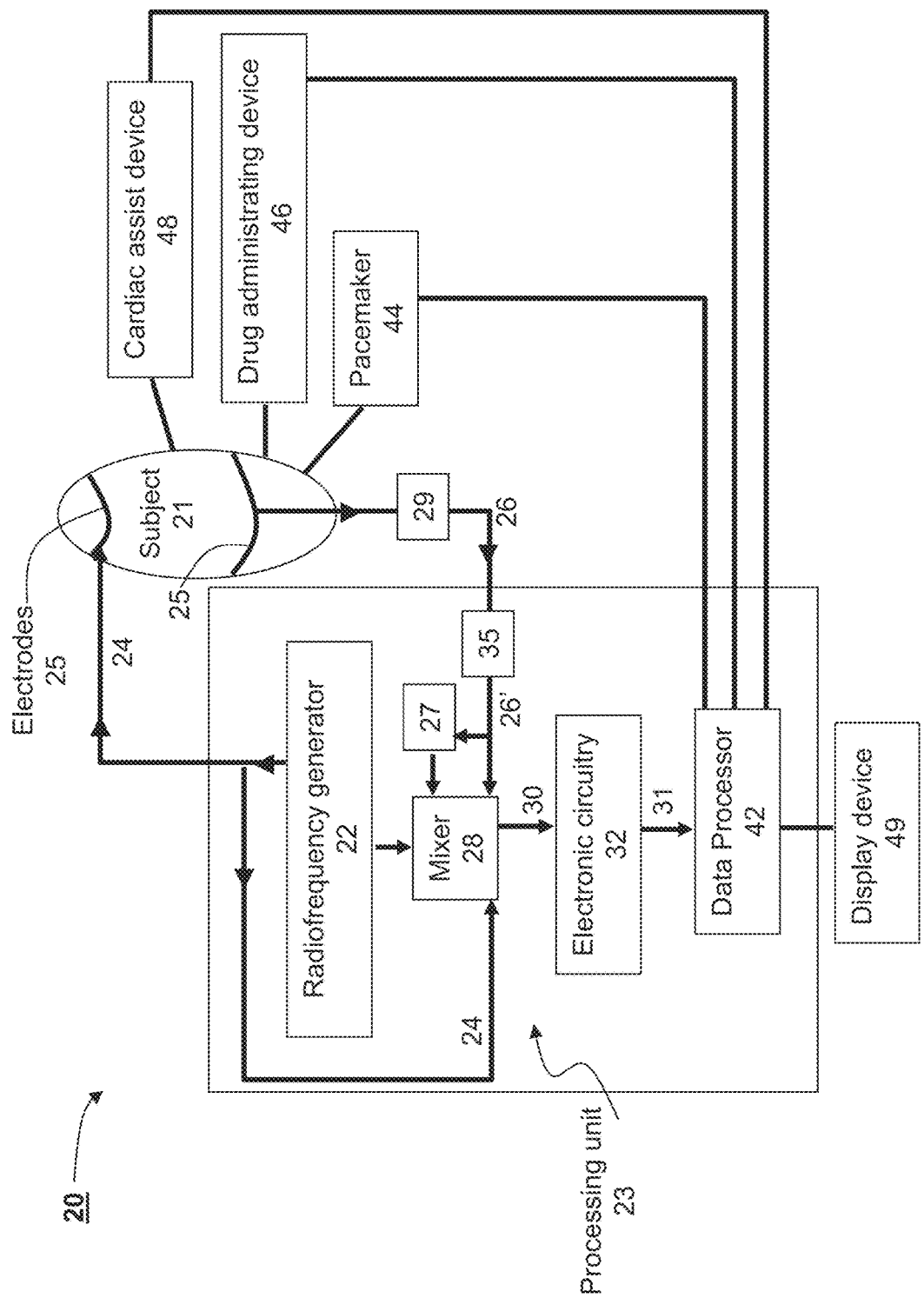
FIG. 2 is a schematic illustration of a system for measuring blood flow in an organ of a subject, according to a preferred embodiment of the present invention.

Reference is now made to FIG. 2, which is a schematic illustration of system 20, according to a preferred embodiment of the present invention. System 20 preferably comprises a radiofrequency generator 22, for generating output radiofrequency signals. Generator 22 may be embodied as any radiofrequency generator, such as, but not limited to, radiofrequency generator 12 of system 10. System 20 further comprises a plurality of electrodes 25, which are connected to the skin of subject 21. Electrodes 25 transmit output radiofrequency signals 24, generated by generator 22 and sense input radiofrequency signals 26 originated from the organ of subject 21.

System 20 preferably comprises a signal processing unit 23 for determining a phase shift $\Delta\varphi$ of signals 26 relative to signals 24. It was discovered by the Inventor of the present invention that the phase shift of the input signals, as received from the organ, relative to the output signals as generated by generator 22, is indicative of the blood flow in the organ. Thus, according to the presently preferred embodiment of the invention the blood flow is determined using the phase shift.

The advantage of using $\Delta\varphi$ for determining the blood flow is that the relation between the blood flow and $\Delta\varphi$ depends on fewer measurement-dependent quantities as compared to prior art determination techniques (e.g., system 10) in which the impedance is used. Specifically, it was found by the Inventor of the present invention that there is a linear relationship between $\Delta\varphi$ and the blood flow, with a proportion coefficient comprising the systolic ejection time, T. For example, the stroke volume SV can be calculated using the relation SV=const.×T×$\Delta\varphi$, and the cardiac output CO can be calculated using the relation CO=const.×T×$\Delta\varphi$×HR, where HR is the heart rate of the subject (e.g., in units of beats per minutes), and "const." a constant which can be found, for example, using a calibration curve. As will be appreciated by one ordinarily skilled in the art, the absence of L and $Z_0$ from the formulae for SV and CO significantly reduces the uncertainty in the obtained values because there is no entanglement between the obtained values and errors associated with the measurement of L and $Z_0$.

According to a preferred embodiment of the present invention signal processing unit 23 comprises an envelope elimination unit 35 which reduces or, more preferably, eliminates amplitude modulation of signals 26. Optionally and preferably unit 35 maintains the phase modulation of signals 26. Signals generated by unit 23 are designated in FIG. 2 by numeral 26'. The input to envelope elimination unit 35 (signals 26) typically carries a substantial amount of AM noise, which can be described, without limitation as a signal $v_{26}$=v(t)cos($\omega$t+$\varphi$(t)), which contains both phase and amplitude modulation. According to a preferred embodiment of the present invention unit 35 generates signals (signals 26') having a substantial constant envelope, e.g., $v_{26}$=$v_0$ cos($\omega$t+$\varphi$(t)), where $v_0$ is substantially a constant. Signals 26' thus represent the phase (or frequency) modulation of signal 26. Signal 26' may be created, for example, using a limiter amplifier which amplifies signals 26 and limits their amplitude such that the amplitude modulation is removed. The advantage of the removal of the amplitude modulation is that it allows a better determination of the phase shift $\Delta\varphi$ between the input and output signals.

The phase shift can be determined for any frequency component of the spectrum of radiofrequency signals received from the organ. For example, in one embodiment, the phase shift is preferably determined from the base frequency component, in another embodiment the phase shift is preferably determined from the second frequency component, and so on. Alternatively the phase shift can be determined using several frequency components, e.g., using an appropriate averaging algorithm.

Processing unit 23 preferably comprises a mixer 28, electrically communicating with generator 22 and at least a portion of electrodes 25, for mixing signals 24 and signals 26', so as to provide a mixed radiofrequency signal 30 being indicative of the blood flow. Signals 24 and 26' may be inputted into mixer 28 through more than one channel, depending on optional analog processing procedures (e.g., amplification) which may be performed prior to the mixing.

For example, in one embodiment, both signals 24 and 26 may be inputted into mixer 28 directly from the terminals that are used for transmitting the signals to and from electrodes 25. In another embodiment, signal 26 may be inputted via an additional unit 27, which is designed for processing signal 26. In an additional embodiment, signal 24 may be inputted from generator 22 where certain analog processing procedures are performed prior to the mixing.

Mixer 28 may be any known radiofrequency mixer, such as, but not limited to, double-balanced radiofrequency mixer and unbalanced radiofrequency mixer. According to a preferred embodiment of the present invention, mixed radiofrequency signal 30 is composed of a plurality of radiofrequency signals, which may be, in one embodiment, a radiofrequency sum and a radiofrequency difference. A sum and a difference may be achieved, e.g., by selecting mixer 28 so that signals 24 and signals 26 are multiplied thereby. Since a multiplication between two frequencies is equivalent to a frequency sum and a frequency difference, mixer 28 outputs a signal which is composed of the desired radiofrequency sum and radiofrequency difference.

One ordinarily skilled in the art would appreciate that the advantage in the production of a radiofrequency sum and a radiofrequency difference is that whereas the radiofrequency sum includes both the signal, which is indicative of the blood flow and a considerable amount of electrical noise, the radiofrequency difference is approximately noise-free.

Thus, the present invention provides an efficient technique for minimizing the electrical noise being associated with such an involved measurement in which the effect of interest is smaller than the measured quantity by about 2-4 orders of magnitude.

According to a preferred embodiment of the present invention system 20 further comprises electronic circuitry 32, which filters out a portion of signal 30 so that a remaining portion 31 of signal 30 is characterized by a substantially increased signal-to-noise ratio.

Reference is now made to FIG. 3, which is a schematic illustration of circuitry 32. According to a preferred embodiment of the present invention circuitry 32 comprises a low pass filter 34 to filter out the high frequency content of signal 30. Low pass filter 34 is particularly useful in the embodiment in which mixer 28 outputs a sum and a difference, where low pass filter filters out the radiofrequency sum and leaves the radiofrequency difference, which, as stated, is approximately noise-free.

Low pass filter 34 may be designed and constructed in accordance with the radiofrequency difference of a particular system which employs system 20. A judicious design of filter 34 substantially reduces the noise content of remaining portion 31. In a conventional bioimpedance system, for example, a substantial amount of the noise of the received signal is folded into the remaining signal, which is thus characterized by a bandwidth of about 2 kilohertz. It has been found by the inventors of the present invention that by including output radiofrequency signal 24 and by mixing it with input radiofrequency signal 26, the noise in the resulting signal is characterized by a bandwidth that is at least one order of magnitude below the noise bandwidth of conventional systems.

According to a preferred embodiment of the present invention, mixer 28 and circuitry 32 are designed and constructed for increasing the signal-to-noise ratio by at least 20 dB, more preferably by 25 dB, most preferably by 30 dB.

Circuitry 32 preferably comprises an analog amplification circuit 36 for amplifying remaining portion 31 of signal 30. The construction and design of analog amplification circuit 36 is not limited, provided circuit 36 is capable of amplifying signal 31. A non limiting example of amplification circuit 36 is further detailed herein below in the Examples section that follows.

According to a preferred embodiment of the present invention circuitry 32 further comprises a digitizer 38 for digitizing signal 31. The digitization of signal 31 is useful for further digital processing of the digitized signal, e.g., by a microprocessor. Additionally and preferably, circuitry 32 comprises a differentiator 40 (either a digital differentiator or an analog differentiator) for performing at least one time-differentiation of the measured impedance to obtain a respective derivative (e.g., a first derivative, a second derivative, etc.) of the impedance and/or hemodynamic reactance. Differentiator 40 may comprise any known electronic functionality (e.g., a chip) that is capable of performing analog or digital differentiation. The time-derivative of the impedance is useful, for example, for measuring stroke volume or cardiac output, as further detailed hereinafter.

Referring now again to FIG. 2, according to a preferred embodiment of the present invention system 20 further comprises a data processor 42 for calculating at least one quantity using signal 31. Many blood-volume related quantities may be calculated, such as, but not limited to, a stroke volume, a cardiac output and a brain intra luminal blood volume. System 20 may further comprise a display device 49 for displaying the blood flow and other information, preferably as a function of time.

According to a preferred embodiment of the present invention system 20 further comprises a detector 29 for detecting a voltage drop on a portion of the body of subject 21 defined by the positions of electrodes 25. In response to the detected voltage, detector 29 preferably generates signals which are indicative of impedance of the respective portion of the body. In this embodiment, the stroke volume can be calculated using $(dZ/dt)_{max}$, as further detailed hereinabove. Knowing the stroke volume, the cardiac output is calculated by multiplying the stroke volume by the heart rate of the subject. More preferably, detector 29 generates signals which are indicative of a hemodynamic reactance, X.

As used herein, "hemodynamic reactance" refers to the imaginary part of the impedance. Techniques for extracting the imaginary part from the total impedance are known in the art. Typically, such extraction is performed at hardware level but the use of algorithm at a software level is not excluded from the scope of the present invention. As will be appreciated by one of ordinary skill in the art, the hemodynamic reactance can be used for determining the aforementioned phase shift $\Delta\varphi$.

The blood flow determination provided by system 20 may be used both for diagnostic and for treatment. Hence, according to a preferred embodiment of the present invention, system 20 may further comprise a pacemaker 44, communicating with data processor 42. In this embodiment, data processor 42 is preferably programmed to electronically control pacemaker 44 in accordance with the calculated quantity. For example, in one embodiment, data processor 42 calculates the cardiac output and sends signals to pacemaker 44 which controls, substantially in real-time, the heart rate of subject 21, so as to improve the cardiac output.

Additionally or alternatively, system 20 may also comprise a cardiac assist device 48, preferably constructed and design for increasing the cardiac output. Cardiac assist devices are known in the art and typically comprise a reinforcing member which restricts an expansion of a portion of the heart tissue, so that the cardiac output is increased. In this embodiment, data processor 42 is preferably programmed to electronically control device 48 in accordance with the calculated cardiac output, so that both the determination and the improvement of the cardiac output are automatically performed by system 20.

According to a preferred embodiment of the present invention system 20 may comprise a drug administrating device 46, communicating with data processor 42. Device 46 serves for administrating drugs to subject 21. In this embodiment, data processor 42 is preferably programmed to electronically control device 46, in accordance with the value of the calculated quantity. For example, if the calculated quantity is the brain intra luminal blood volume, then depending on the value of the blood volume, data processor 42 sends signal to device 46 and thereby controls the amount and/or type of medications administered to subject 21.

The number of electrodes which are connected to subject 21 is preferably selected so as to substantially decouple the input radiofrequency signals from undesired effects, such as, but not limited to, a posture changes effect, a respiration effect, a motion effect and the like.

For any number of electrodes which are used in accordance with a preferred embodiment of the present invention, at least a portion of the electrodes are designed and constructed to so as to have a substantial constant sensitivity to electrical signals transmitted through electrodes, irrespectively of an orientation of the electrodes on the subject.

Reference is now made to FIGS. 4a-h, which are schematic illustrations of electrodes 25 (FIGS. 4c, 4d, 4g and 4h) and the respective positions to which electrodes 25 are attached (FIGS. 4a, 4b, 4e and 4f), according to a preferred embodiment of the present invention. FIGS. 4c and 4g shows the inner side of electrode 25 and FIGS. 4d and 4h shows the outer side of electrode 25.

Hence, electrodes 25 preferably comprise at least one elongated conducting material 50 designed and constructed to wind at least a portion of an external organ, which may be, for example, a chest, a hip, a thigh, a neck, a head, an arm, a forearm, an abdomen, a gluteus, a leg, a foot and the like. Optionally, electrode 25 may also comprise an attaching material 52 (e.g., velcro, glue and the like) for facilitating the attachment of electrode 25 to subject 21.

It is recognized that conventional spot electrodes, which are used, e.g., in bioimpedance systems (see, e.g., FIG. 1), are sensitive to the particular position to which the electrodes are attached. This sensitivity is particularly disadvantageous in bioimpedance systems where the signal-to-noise ratio is intrinsically small and the fluctuations caused by such artifacts may be comparable to the entire effect which is to be measured. It is further recognized that the problems associated with the sensitivity to small displacements are aggravated when the number of spot electrodes increases. Specifically, with a tetrapolar array of FIG. 1, there are eight spot electrodes each of which contribute to the sensitivity to small displacements, hence increasing the uncertainty of the final measurement.

The advantage of the use of electrodes 25, according to the presently preferred embodiment of the invention, is that the signal which is received from the body of subject 21 does not depend on small displacements of the electrodes. In addition, as further detailed herein below, the number of electrodes which are used is substantially smaller than the number which is used in conventional systems. It will be appreciated that smaller number of electrodes (i) reduces the uncertainty factor; (ii) is more easy to attach; and (iii) more comfortable to the patient.

Referring to FIGS. 4a, in one embodiment, one electrode is attached to the neck of subject 21 and two electrodes are attached below the heart. This embodiment may be used, for example, for measuring and determining stroke volume and cardiac output. It is it be understood, however, that other configurations are not excluded for the purpose of determining stroke volume and cardiac output. Specifically, two electrodes may be used. Nevertheless, it was found by the inventors of the present invention, that the motion effects with the use of three electrodes were less pronounced than with the use of two electrodes. The preferred electrodes to be used in this embodiment are shown in FIGS. 4c (inner side) and 4d (outer side).

Referring to FIG. 4b, in another embodiment, two electrodes are attached to the neck of subject 21 and two electrodes are attached below the heart. This embodiment may be used, for example, for measuring and determining stroke volume and cardiac output. As demonstrated in the Examples section that follows, the quality of the results is significantly enhanced with the use of four electrodes. The preferred electrodes to be used in this embodiment are shown in FIGS. 4c (inner side) and 4d (outer side).

Referring to FIGS. 4e-h, in an additional embodiment, two electrodes formed on a single elongated strip may be used for the purpose of determining brain intra luminal blood volume. Specifically, as shown in FIG. 4e, a single strip (thus, two electrodes) may be wound around the forehead of subject 21, or alternatively and preferably, two strips (thus, four electrodes) may be adjacently wound around the forehead of subject 21.

It is to be understood that any number of electrodes or connection configurations are not excluded from the present invention. For example, the electrodes shown in FIG. 4c-d, the electrodes shown in FIG. 4g-h or any other electrodes may be used, in any combination, for measuring blood flow in any artery of the body, such as, but not limited to, the external carotid artery, the internal carotid artery, the ulnar artery, the radial artery, the brachial artery, the common iliac artery, the external iliac artery, the posterior tibial artery, the anterior tibial artery, the peroneal artery, the lateral plantar artery, the medial plantar artery and the deep plantar artery.

When system 20 is used together with other systems it is desired to minimize the area occupied by electrodes 25 so as not to interfere the operation of the other systems. For example, in intensive care units, the subjects are oftentimes connected to ECG leads, arterial line, central venous line, brain stem evoked response equipment, chest tubes, GI tube, intravenous and the like. In such or similar situations system 20 preferably comprises smaller electrodes, which are illustrated in FIGS. 4i-L.

Figure 4J:
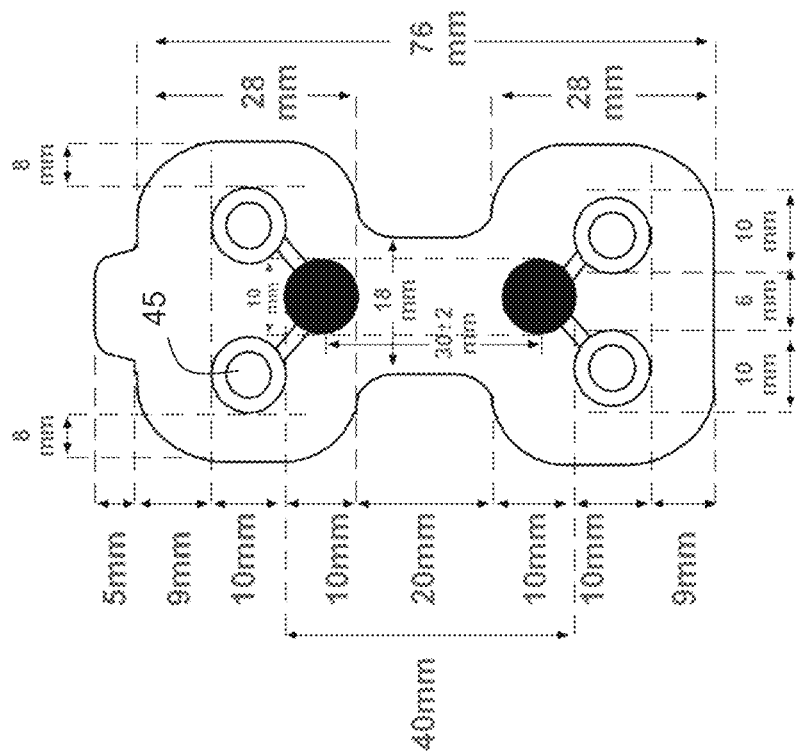
FIGS. 4*i*-L are schematic illustrations of electrode stickers, according to a preferred embodiment of the present invention.
Figure 4I:
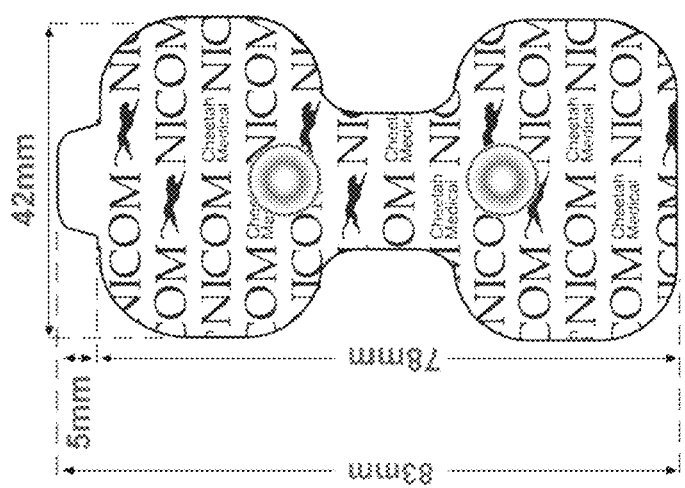

FIGS. 4i-j show a back side (FIG. 4i) and a front side (FIG. 4j) of a sticker which can be used for transmitting and sensing the radiofrequency signals, according to a preferred embodiment of the present invention. The sticker comprises electrical contacts 45 being as fixed and predetermined distance therebetween, thus reducing any the effect of variable inter-electrode distance on the measurement.

Figures 4K, 4L:
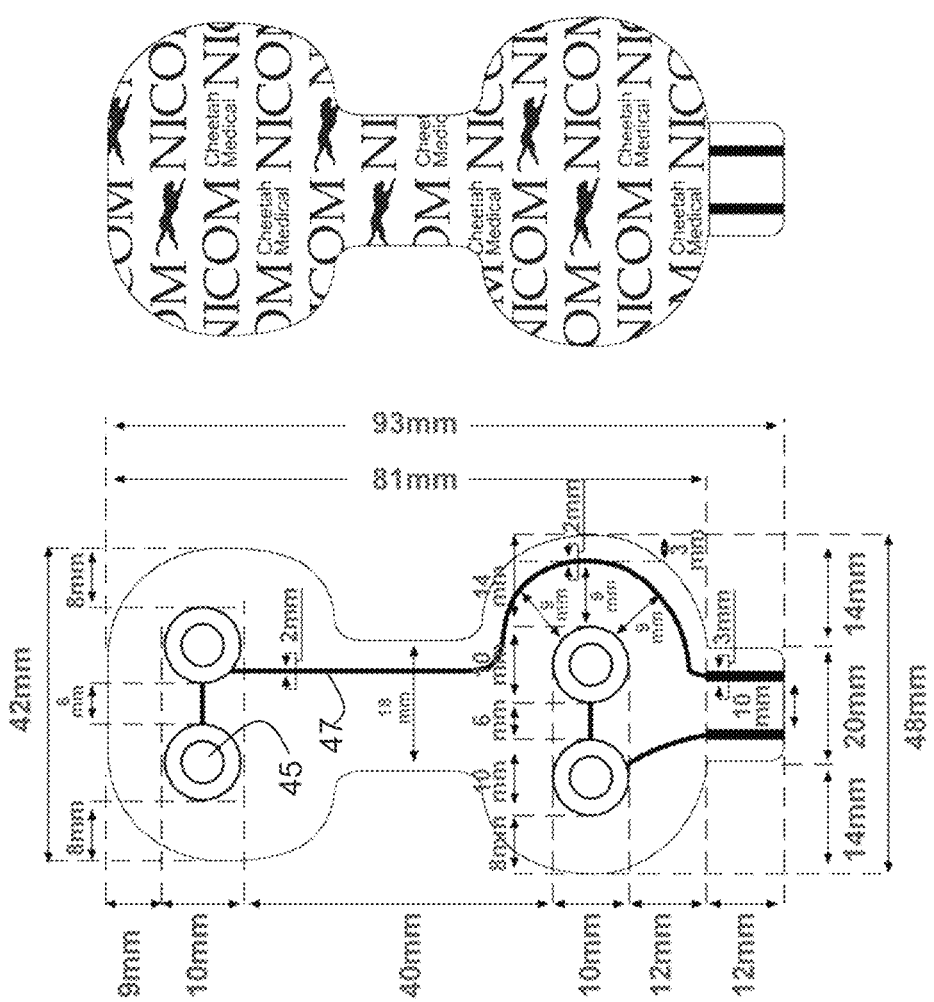

FIGS. 4K-L show a front side (FIG. 4K) and a back side (FIG. 4L) of another sticker which is similar to the sticker shown in FIGS. 4i-j, with the exception that the sticker of FIGS. 4K-L can be connected to system 20 using a single line because the electrical contacts on the sticker are interconnected by an internal line 47.

According to another aspect of the present invention there is provided an apparatus for determining blood flow in an organ of a subject, generally referred to herein as apparatus 60. Apparatus 60 enjoys the property of an enhanced signal-to-noise ratio and, as such, apparatus 60 may be used in combination with any blood flow measuring system, e.g., system 20.

Reference is now made to FIG. 5, which is a schematic illustration of apparatus 60. Apparatus 60 preferably comprises electronic circuitry having an envelope elimination unit (e.g., unit 35) for reducing or eliminate amplitude modulation of the input radiofrequency signals as further detailed hereinabove. Apparatus further comprises a signal processing unit (e.g., unit 23) for determining the blood flow in the organ. According to a preferred embodiment of the present invention the signal processing unit determines the phase shift of the input signals relative to the output signals as further detailed hereinabove.

Apparatus 60 may further comprise mixer 28 for mixing signals 24 and signals 26', so as to provide a mixed radiofrequency signal as further detailed hereinabove. As illustrated in FIG. 5, signals 24 and 26 may be inputted into mixer 28 either directly from the terminals, which are used for transmitting the signals to and from the organ, or via unit 22. The electronic circuitry of apparatus 60 preferably filters out a portion of the mixed radiofrequency signal such that the remaining portion of the signal is characterized by a substantially increased signal-to-noise ratio as detailed above.

According to an additional aspect of the present invention there is provided an apparatus 90 for calculating blood flow in an organ of a subject from the output and input radiofrequency signals.

Figure 6:
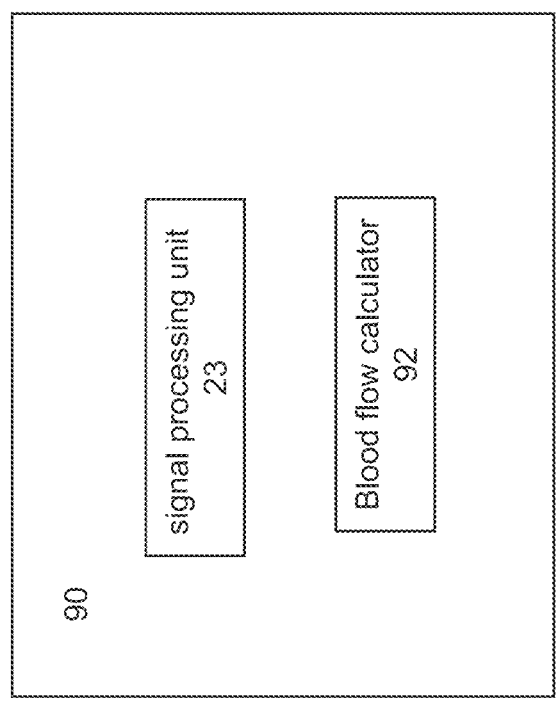
FIG. 6 is a schematic illustration of an apparatus for calculating blood flow, according to a preferred embodiment of the present invention.

Reference is now made to FIG. 6 which is a simplified illustration of apparatus 90. Apparatus 90 preferably comprising a signal processing unit (e.g., unit 23) for determining a phase shift of the input radiofrequency signals relative to the output radiofrequency signals, and a blood flow calculator 92 which calculates the blood flow using the phase shift. Calculator 92 preferably calculates the blood flow using a linear relation between the blood flow and the phase shift, as further detailed hereinabove.

Figure 7:
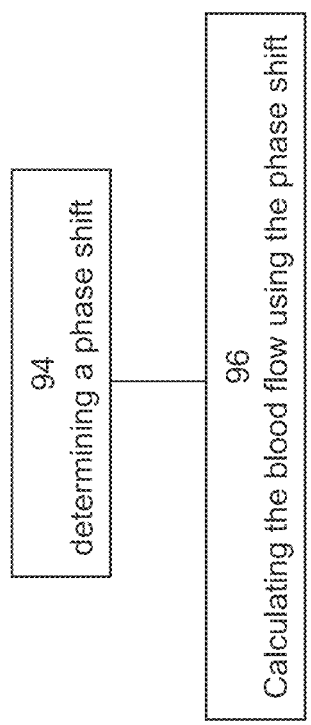
FIG. 7 is a flowchart diagram of a method of calculating blood flow, according to a preferred embodiment of the present invention.

According to yet another aspect of the present invention there is provided a method of calculating the blood flow blood. The method comprises the following steps, which are illustrated in the flowchart of FIG. 7. In a first step of the method, designated by Block 94, the phase shift of the input signals relative to the output signals is determined, and in a second step, designated by Block 96 the phase shift is used for calculating the blood flow, e.g., using a linear relationship between the phase shift and the blood flow.

Figure 8:
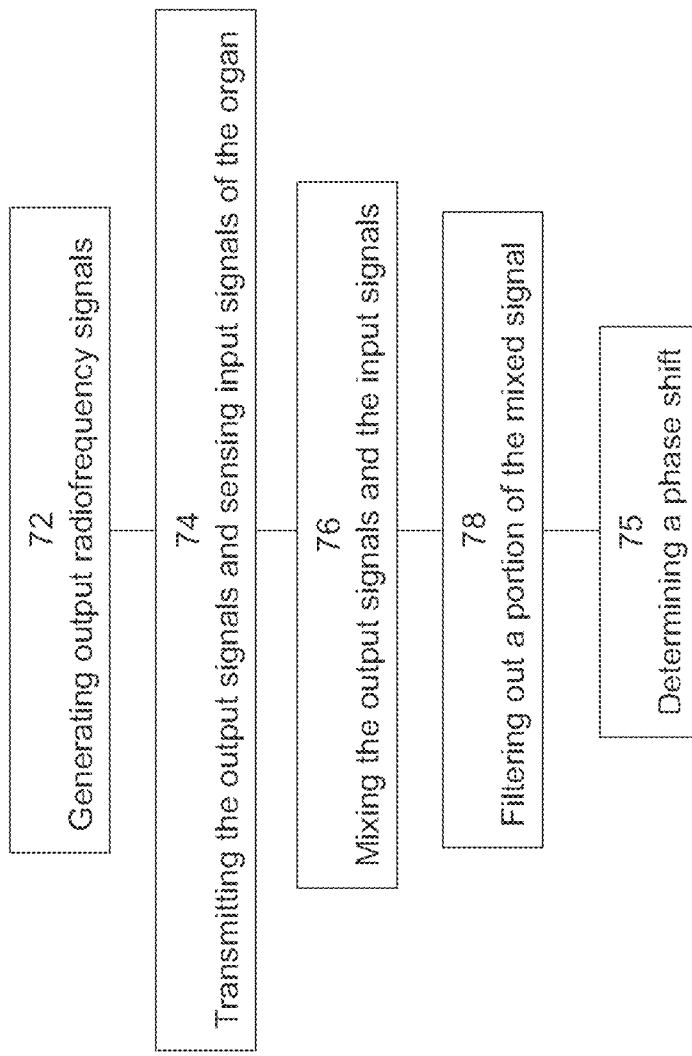
FIG. 8 is a flowchart diagram of a method of measuring blood flow in an organ of a subject, according to a preferred embodiment of the present invention.

According to still another aspect of the present invention there is provided a method of measuring blood flow in an organ of a subject, the method comprising the following steps, which are illustrated in the flowchart of FIG. 8. Hence, in a first step, designated by Block 72, output radiofrequency signals are generated, e.g., by a radiofrequency generator. In a second step, designated by Block 74, the output radiofrequency signals are transmitting to the organ and input radiofrequency signals are sensed of the organ, e.g., by an array of electrodes.

In a third step, designated by Block 75, a phase shift of the input signals relative to said output signals is determined and used for calculating the blood flow as further detailed hereinabove. In optional steps, designated in FIG. 8 by Blocks 76 and 78, the output radiofrequency signals and the input radiofrequency signals are mixed (Block 76) to provide a mixed signal, and a portion of the mixed signal is filtered out (Block 78) so as to substantially increase the signal-to-noise ratio of a remaining portion thereof as further detailed hereinabove.

According to a preferred embodiment of the present invention, the method may further comprise the following optional steps, where each optional step may be performed independently of the other optional steps in any combination or order. Hence, in one optional step the remaining portion of the mixed radiofrequency signal is analogically amplified; in another optional step, the remaining portion of mixed radiofrequency signal is digitized; in an additional optional step at least one quantity (e.g., a stroke volume, a cardiac output and a brain intra luminal blood volume) is calculated; in still an additional step at least one time-differentiation is performed, as further detailed hereinabove.

Following are technical preferred values which may be used for selective steps and parts of the embodiments described above.

As used herein the term "about" refers to ±10%.

The output radiofrequency signals are preferably from about 10 KHz to about 200 KHz in frequency and from about 10 mV to about 50 mV in magnitude; the input radiofrequency signals are preferably about 70 KHz in frequency and about 20 mV in magnitude; a typical impedance which can be measured by the present embodiments is from about 25 Ohms to about 35 Ohms; the resulting signal-to-noise ratio of the present embodiments is at least 40 dB; low pass filter 34 is preferably characterized by a cutoff frequency of about 35 Hz and digitizer 38 preferably samples the signals at a rate of about 1000 samples per second.

Additional objects, advantages and novel features of the present invention will become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

EXAMPLES

Reference is now made to the following examples, which, together with the above descriptions, illustrate the invention in a non limiting fashion.

A prototype of a system for measuring blood flow in an organ of a subject according to the above description was constructed.

The prototype system includes:

(a) a self made radiofrequency generator generating output radiofrequency signals, 70 Khz in frequency and 20 mV in magnitude;

(b) a plurality of electrodes, as described in FIGS. 4b, 4c, 4e and 4f; and (c) a double balanced mixer, purchased from Mini-Circuits, used for providing a radiofrequency sum and a radiofrequency difference, as detailed above.

The prototype system further includes electronic circuitry formed in a printed circuit board. Several electronic circuitries were designed and manufactured, so as to investigate the correlation between the quality of the results, the design of the electronic circuitry and the number of electrodes. The various electronic circuitries are schematically illustrated in FIGS. 9a-d.

Figure 9A:
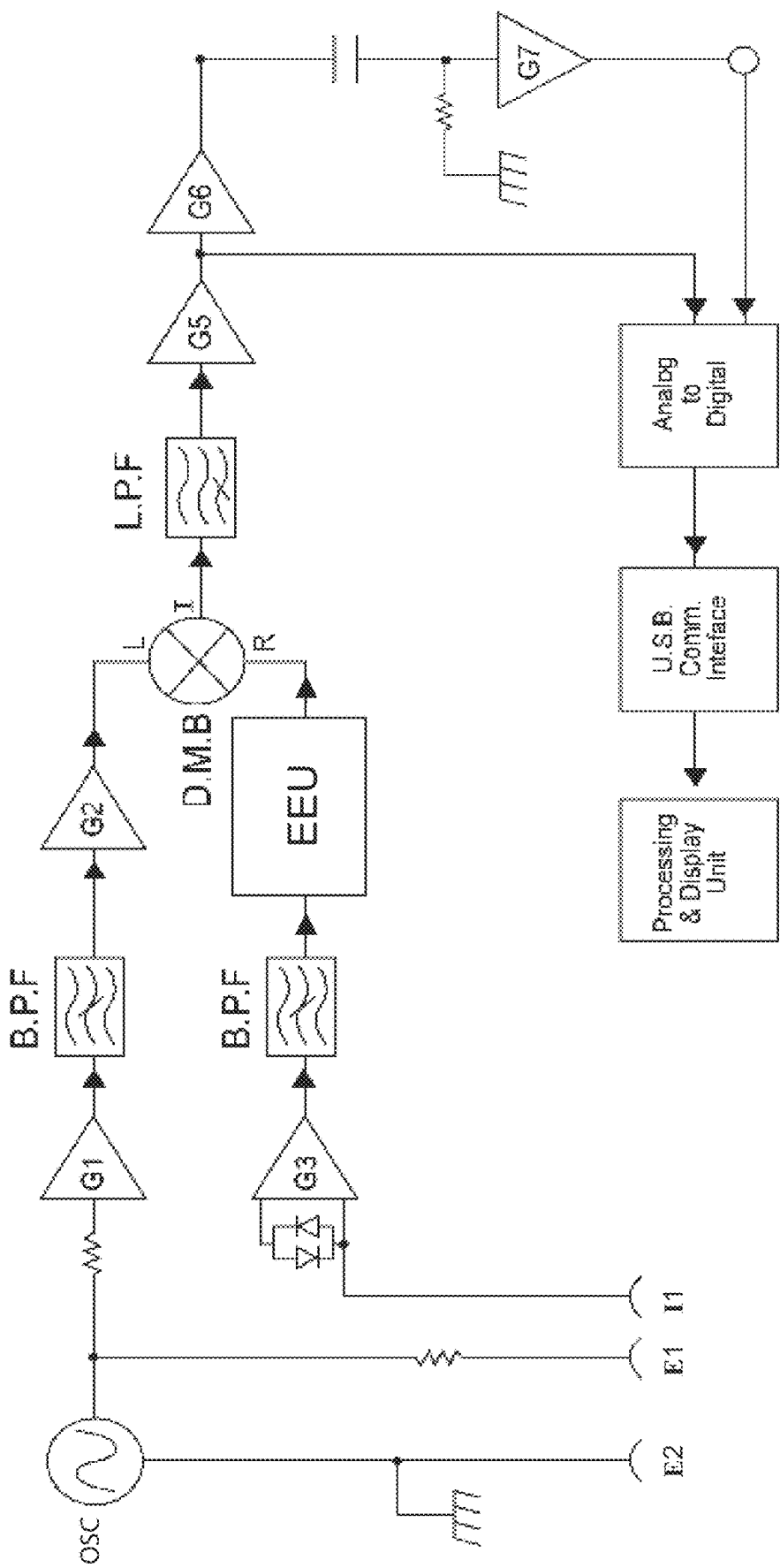
FIG. 9*a* is a block diagram of a printed circuit board for measuring blood flow, using three electrodes.

FIG. 9a shows a block diagram of electronic circuitry to be used with three electrodes (see results of cardiac-output measurements in Example 1, below). The electrodes leads are designated in FIG. 9a by $E_1$, $E_2$ and $I_1$, where the output radiofrequency signals, generated by the radiofrequency generator (designated OSC), are outputted through $E_1$ and $E_2$ and the input radiofrequency signals, as measured of the body are inputted through $I_1$.

The input signals and are channeled through a differential amplifier $G_1$, a band pass filter BPF and a differential amplifier $G_2$. The input signals are channeled through a differential amplifier $G_3$, a band pass filter BPF and an envelope elimination unit EEU. The EEU eliminates the amplitude modulation from the input signal. Both input and output signals are mixed by mixer DMB, to form, as stated, a frequency sum and a frequency difference. A low pass filter LPF filters out the frequency sum and the resulting signal (carrying the frequency difference) is further amplified by additional differential amplifiers $G_5$, $G_6$ and $G_7$. Once amplified, the signal is digitized by an analog to digital digitizer and passed, via a USB communication interface to a processing and display unit.

Figure 9B:
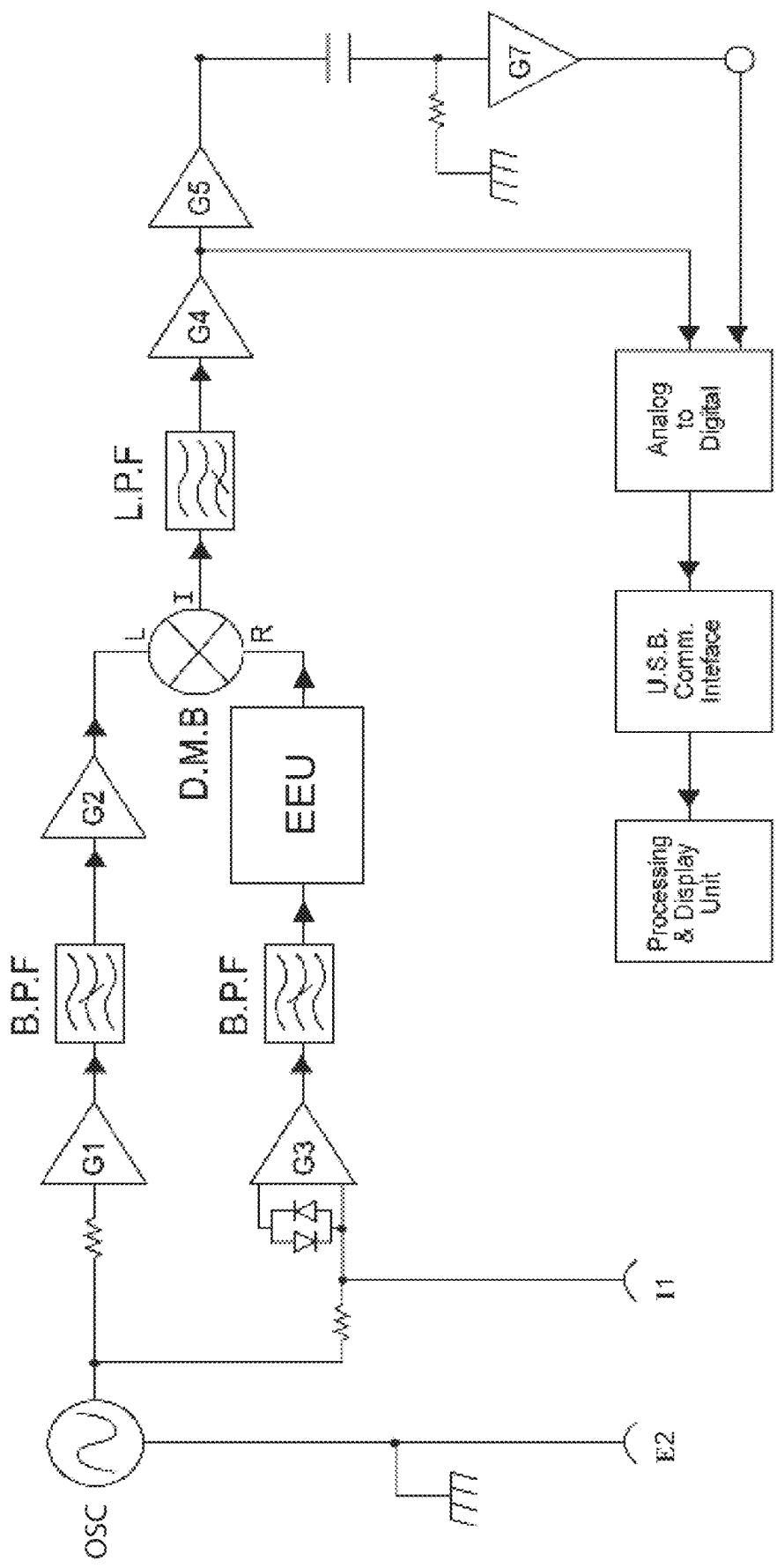
FIG. 9*b* is a block diagram of a printed circuit board for measuring blood flow, using two electrodes.

FIG. 9b shows a block diagram of electronic circuitry to be used with two electrodes of brain intra-luminal blood volume measurements in Example 2, below). As there are only two electrodes $E_2$ and $I_1$ are combined to a single lead $I_1$.

Thus, the output signals and are channeled through a differential amplifier $G_1$, a band pass filter BPF and a differential amplifier $G_2$. The input signals are channeled through a differential amplifier $G_2$, a band pass filter BPF and an envelope elimination unit EEU which eliminates the amplitude modulation from the input signal. Both input and output signals are mixed by mixer DMB, to form the frequency sum and difference. The low pass filter LPF filters out the frequency sum and the resulting signal is further amplified by additional differential amplifiers $G_4$, $G_5$ and $G_6$. As in the case of three electrodes, the signal is digitized by an analog to digital digitizer and passed, via a USB communication interface to a processing and display unit.

Figure 9C:
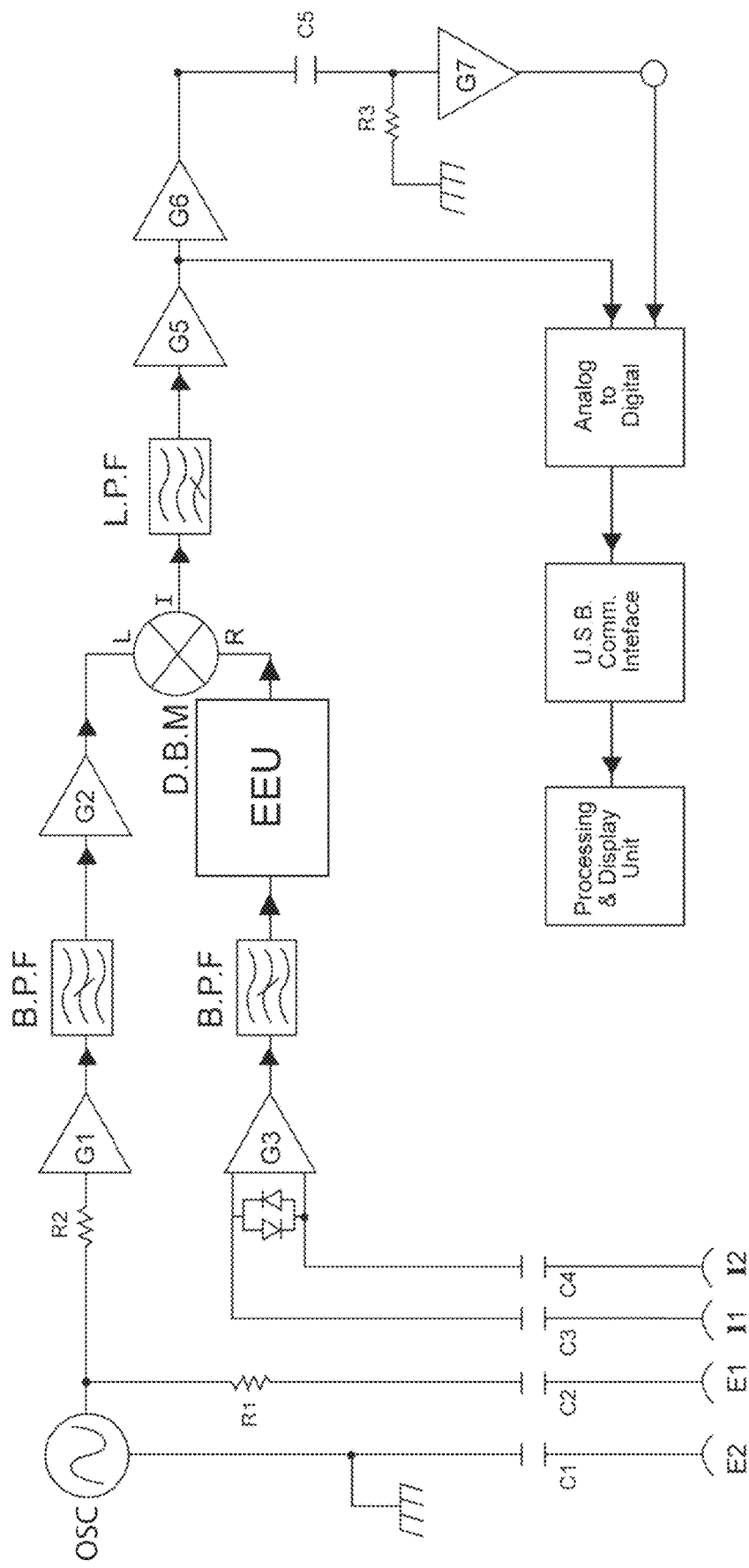
FIG. 9*c* is a block diagram of a printed circuit board for measuring blood flow, using four electrodes.

FIG. 9c shows a block diagram of electronic circuitry to be used with four electrodes (see results of cardiac-output measurements in Example 3 and brain intra-luminal blood volume measurement in Example 4, below). The four leads, designated $E_1$, $E_2$, $I_1$ and $I_2$, where the output radiofrequency signals, generated by radiofrequency generator OSC, are outputted through $E_1$ and $E_2$ and the input radiofrequency signals, as measured of the body are inputted through $I_1$ and $I_2$. In addition, the four leads, $E_1$, $E_2$, $I_1$ and $I_2$ are connected to the body through capacitors designated $C_1$, $C_2$, $C_3$ and $C_4$.

The principles of the circuitry of FIG. 9c are similar to the principles of the circuitry of FIG. 9a with three electrodes. The advantage of the circuitry of FIG. 9c is that by using both input leads $I_1$ and $I_2$ (as opposed to one input lead $I_1$ of FIG. 9a), effects of impedance differences between the electrodes and the body can be minimized Specifically, the influence of the voltage drop $I_1$ and $I_2$ is controlled by the characteristic impedance of the differential amplifier $G_3$, which is selected to be sufficiently large so that any impedance changes due to the contact between the body and the electrode is negligible, compared to the impedance of $G_3$.

Figure 9D:
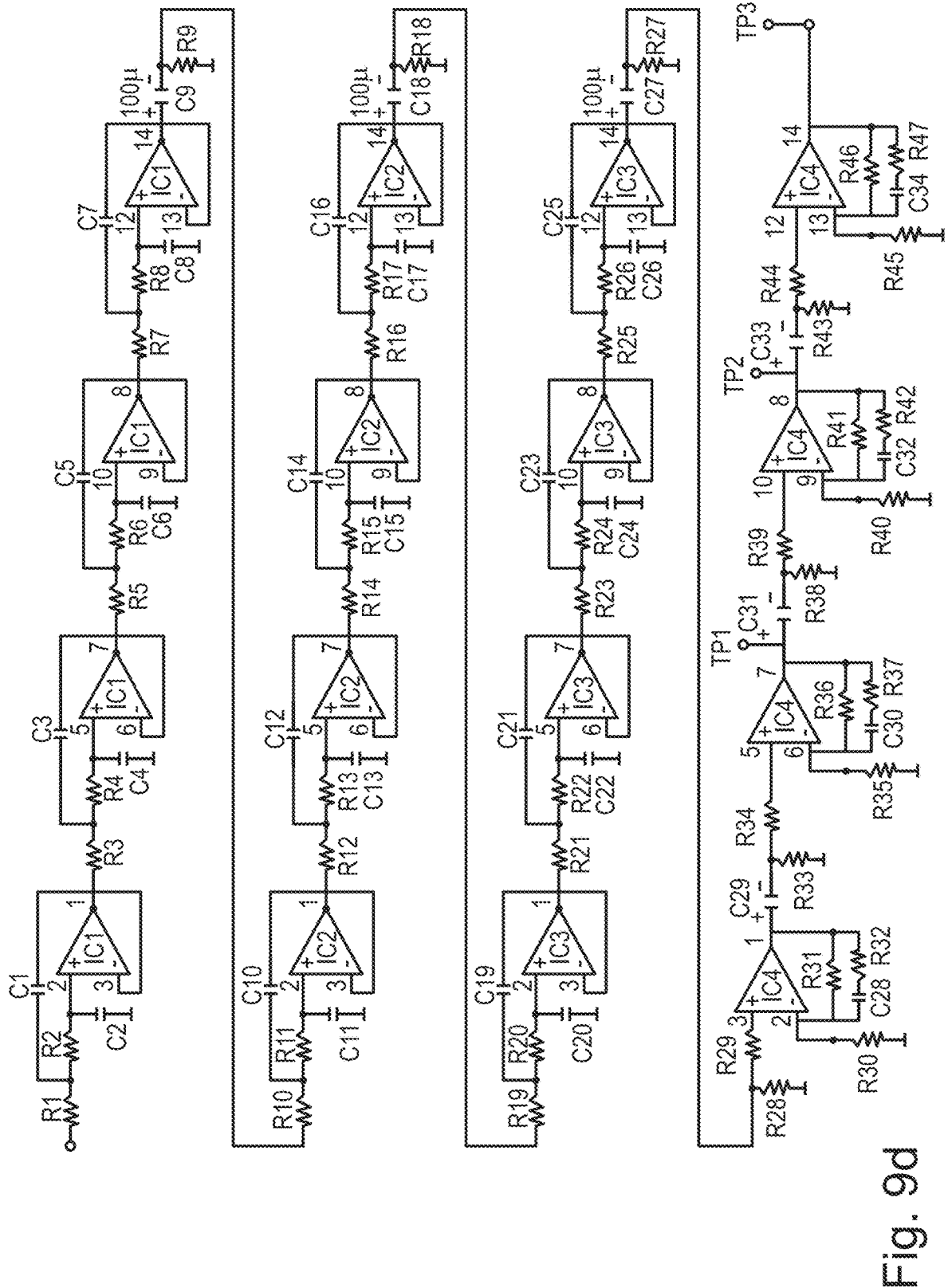
FIG. 9*d* is a block diagram of an analog amplification circuit for amplifying the radiofrequency signal.

FIG. 9d shows a block diagram of the analog amplification circuit, which was used to amplify the radiofrequency signal after the low pass filtering in which the radiofrequency sum was filtered out.

Example 1

Measurement of Stroke Volume and Cardiac Output Using Three Electrodes

Three electrodes were connected to a human subject, as shown in FIG. 4a. The hemodynamic reactance was measured and was used for determining and monitoring (i) stroke volume; and (ii) cardiac output.

Figure 10A:
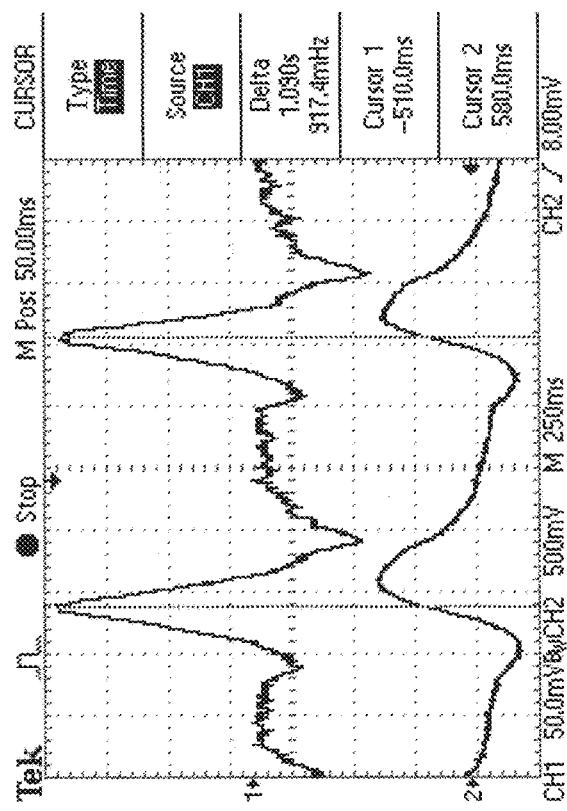
FIGS. 10*a-b* show monitoring results of the change in the hemodynamic reactance and its measured derivative, obtained using a prototype system with three electrodes built according to a preferred embodiment of the present invention, for the purpose of determining stroke volume and cardiac output.
Figure 10B:
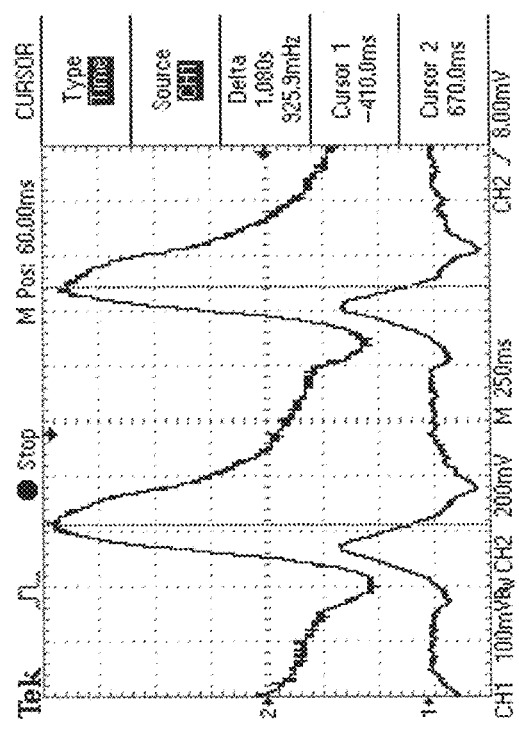

FIGS. 10a-b shows the monitoring results obtained using the prototype system (using the circuitry of FIG. 9a) on a time scale of 250 ms/div. Two waveforms are displayed in each of FIGS. 10a-b, the change in the hemodynamic reactance and its measured time derivative. The waveforms shown in FIG. 10b are in reverse magnification compared to the waveforms shown in FIG. 10a.

Figure 10C:
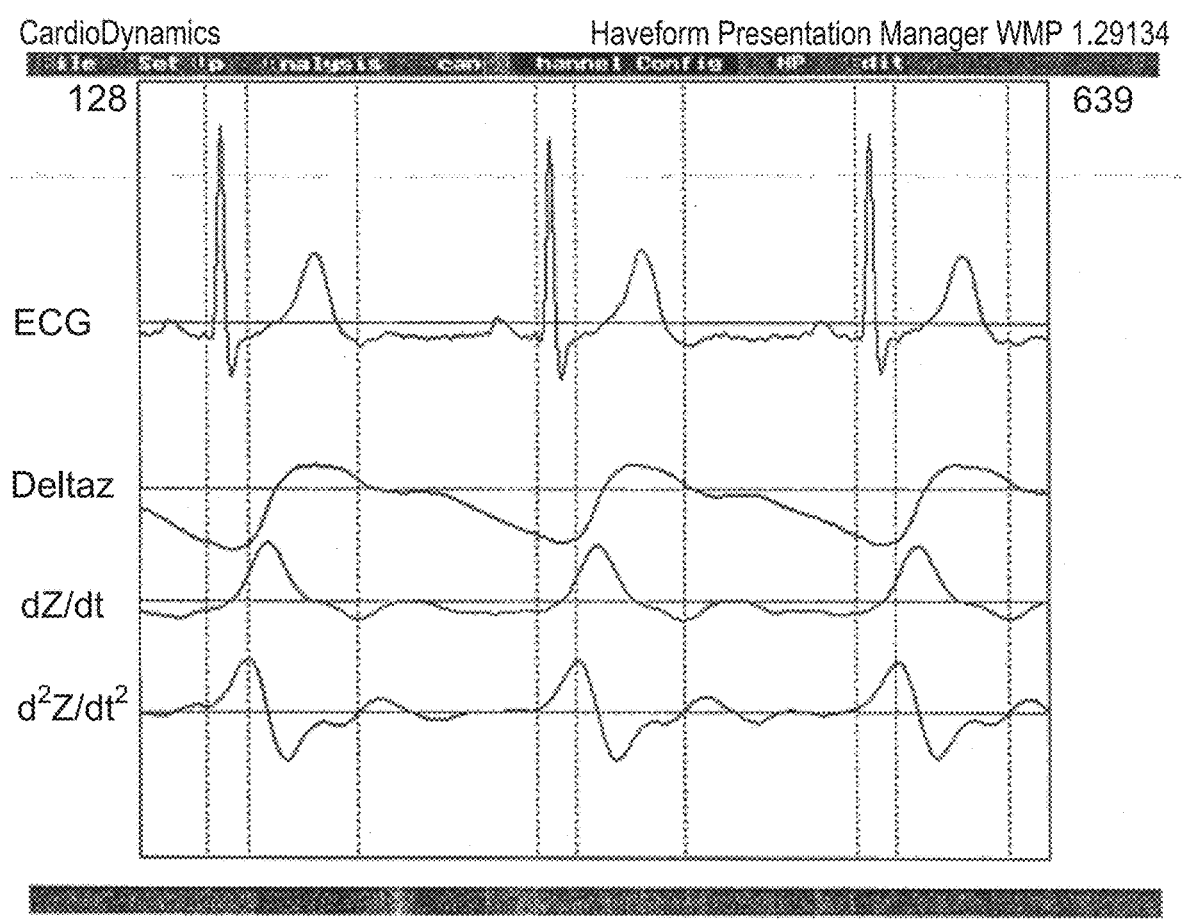
FIG. 10*c* shows monitoring results of the ECG signal, change in the bioimpedance, its first derivative and its second derivative, obtained using a conventional (prior art) system.

For comparison, FIG. 10c shows monitoring results obtained using a conventional system (GE/Cardiodynamic). The waveforms displayed in FIG. 10c, are, from top to bottom, the ECG signal, the change in the bioimpedance, $\Delta Z$, its first derivative, $dZ/dt$ and its second derivative $d^2Z/dt^2$.

The improvement of the signal-to noise ratio of the present invention (FIGS. 10a-b) over the conventional system (FIG. 10c) is vivid. In the prototype system the signal-to-noise ratio was 50 dB, whereas in the conventional system the signal-to-noise ratio was 20 dB.

Example 2

Measurement of Brain Intra Luminal Blood Volume Change and Flow Rate Using Two Electrodes Two electrodes were connected to a human subject, as shown in FIG. 4e. The hemodynamic reactance was measured and was used for determining and monitoring brain intra luminal blood volume change and flow rate.

Figure 11A:
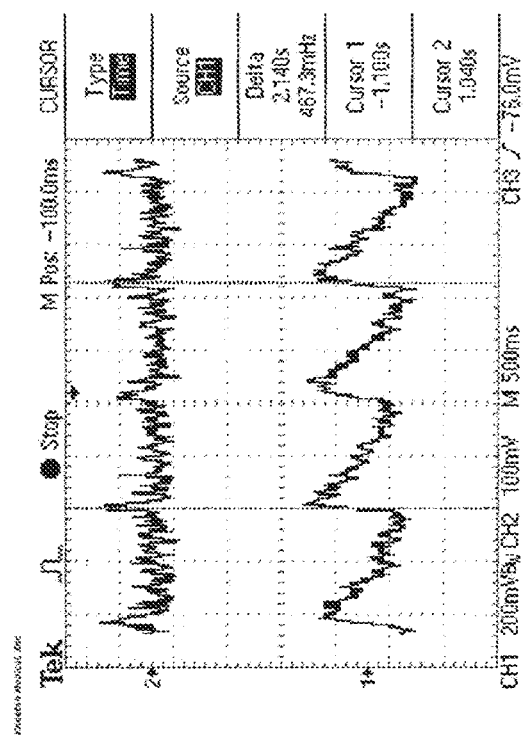
FIGS. 11a-b show monitoring results of the change in the hemodynamic reactance and its measured derivative obtained using the prototype system with two electrodes, built for the purpose of measuring brain intra luminal blood volume change and flow rate.
Figure 11B:
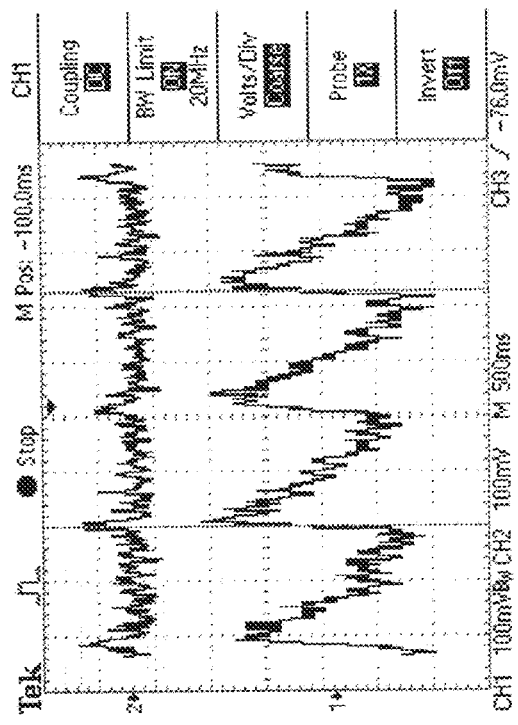

FIGS. 11a-b show the monitoring results obtained using the prototype system (using the circuitry of FIG. 9b) on a time scale of 250 ms/div. Two waveforms are displayed in each of FIGS. 11a-b, the change in the hemodynamic reactance and its measured derivative, where in FIG. 11b, the vertical scale for the curve of the change in the hemodynamic reactance is twice larger than the respective curve in FIG. 11a.

As shown in FIGS. 11a-b, a good signal-to noise ratio of 50 dB was obtained for both quantities. The curves of the present example acquire a sharper peak, as compared to Example 1. This phenomenon is consistent with physiological findings, according to which the resistance to blood flow in the brain is substantially lower than the resistance in the thorax. Thus, in the brain, there is only a small delay in the response to the change of blood flow, as compared to the thorax. The quick response to blood flow is manifested by the measured quantities hence the sharp peaks in the curves of FIG. 11a-b.

Example 3

Measurement of Stroke Volume and Cardiac Output Using Four Electrodes

Four electrodes were connected to a human subject, as shown in FIG. 4b. The hemodynamic reactance was measured and was used for determining and monitoring (i) stroke volume; and (ii) cardiac output.

Figure 12A:
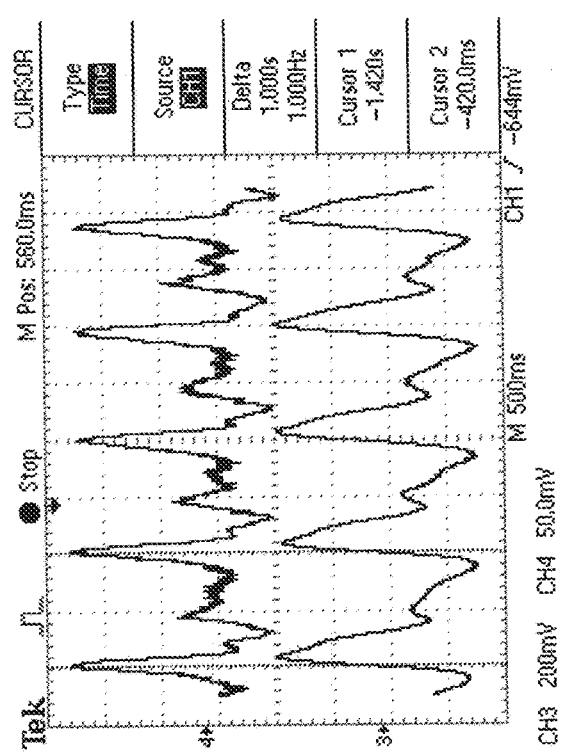
FIG. 12a shows monitoring results of the change in the hemodynamic reactance and its measured derivative, obtained using a prototype system with four electrodes built according to a preferred embodiment of the present invention, for the purpose of determining stroke volume and cardiac output.

FIG. 12a shows the monitoring results obtained using the prototype system (using the circuitry of FIG. 9c) on a time scale of 500 ms/div. Two waveforms are displayed in FIG. 12, the change in the change in the hemodynamic reactance and its measured time derivative.

Figure 12B:
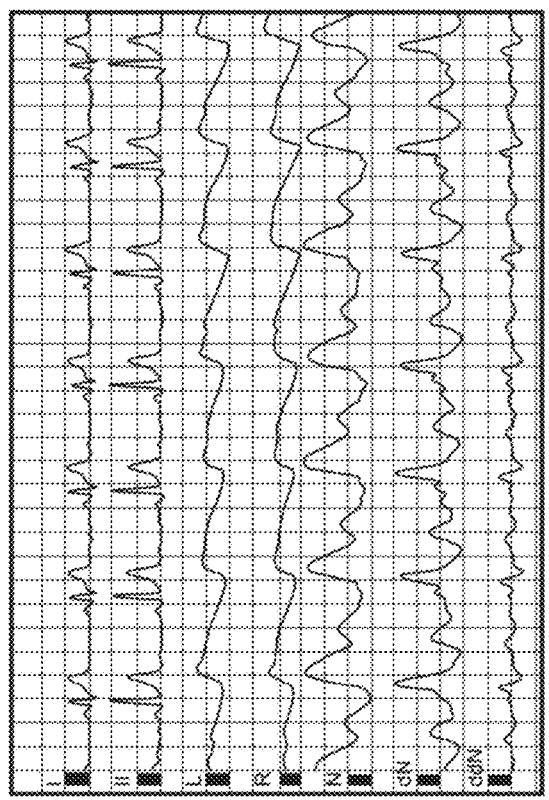
FIG. 12b shows a comparison between data acquired from ECG (two leads), blood wave front (left and right) and CO signal including its first and second derivatives, according to a preferred embodiment of the present invention.

FIG. 12b shows a comparison between the CO signal as calculated from the phase shift $\Delta \varphi$ according to the embodiments of the invention, and data acquired from other channels. From top to bottom, FIG. 12b shows, as a function of time: ECG lead I (designated I In FIG. 12b), ECG lead II (designated II), left blood wave front (L), right blood wave front (R), CO signal (N), first derivative of the CO signal (dN) and second derivative of the CO signal (ddN). As shown in FIG. 12b, the embodiments of the present invention provide a high quality signal which enjoys an enhance signal-to-noise ratio and is indicative of the blood flow.

Comparing FIGS. 12a-b and FIGS. 10a-b, the use of four electrodes (and the electronic circuitry of FIG. 9c) significantly improves of the quality of the results.

Example 4

Measurement of Brain Intra Luminal Blood Volume Change and Flow Rate Using Four Electrodes Two electrodes were connected to a human subject, as shown in FIG. 4f. The hemodynamic reactance was measured and was used for determining and monitoring brain intra luminal blood volume change and flow rate.

Figure 13:
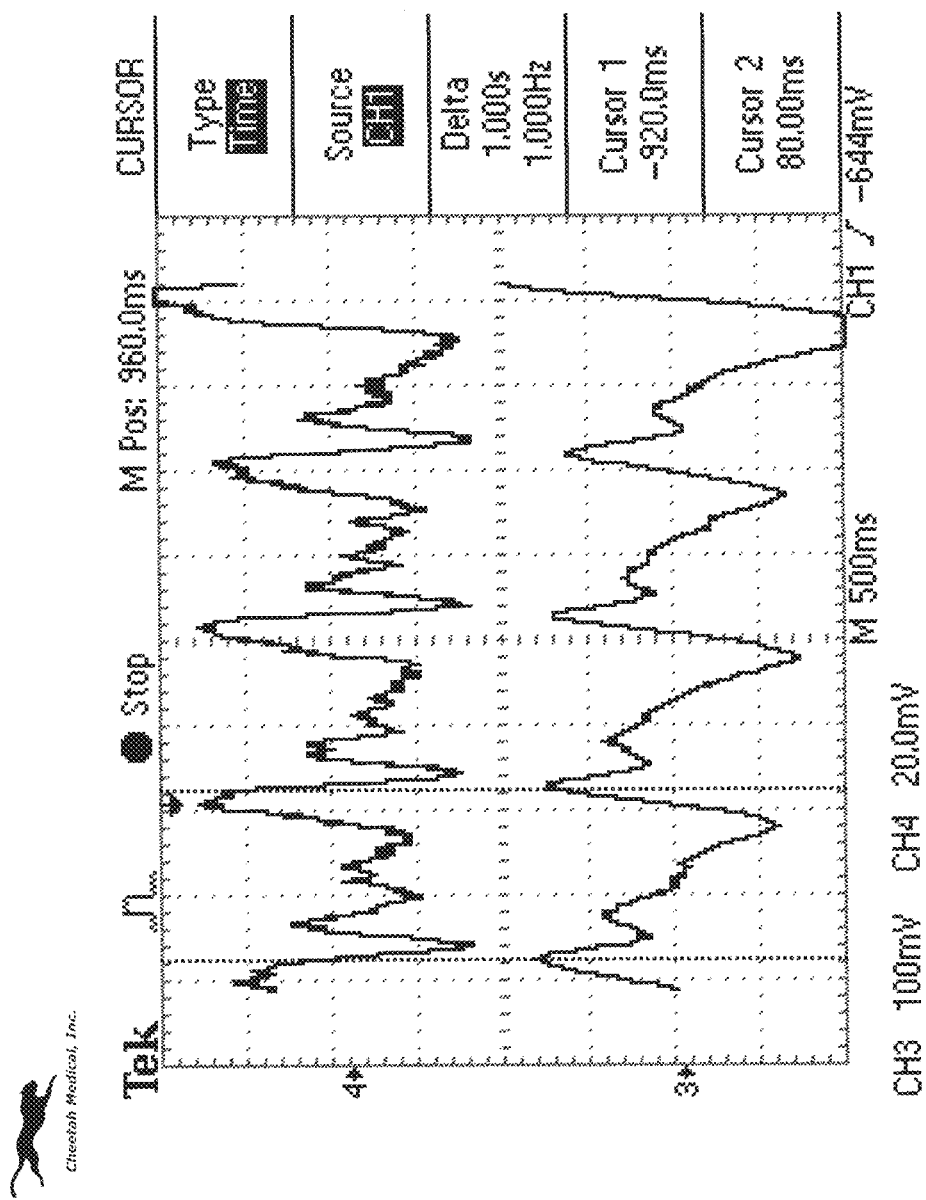
FIG. 13 show monitoring results of the change in the hemodynamic reactance and its measured derivative obtained using the prototype system with four electrodes, for the purpose of measuring brain intra luminal blood volume change and flow rate.

FIG. 13 show the monitoring results obtained using the prototype system (using the circuitry of FIG. 9c) on a time scale of 500 ms/div. Two waveforms are displayed in FIG. 13, the change in the hemodynamic reactance and its measured derivative.

As shown in FIG. 13, a good signal-to noise ratio of 50 dB was obtained for both quantities. As in Example 3 above, a comparison between FIGS. 13 and 9a-b, reveal a significant improvement of the present example (four electrodes and the circuitry of FIG. 9c) over Example 2 (two electrodes and the circuitry of FIG. 9b).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of determining a blood flow quantity in an organ of a subject, the method comprising:
   placing a plurality of electrodes on the organ;
   transmitting by a portion of said electrodes output radiofrequency signals to the organ;
   receiving by another portion of said electrodes input radiofrequency signals from the organ;
   by a dedicated electronic circuitry, reducing or eliminate amplitude modulation of said input radiofrequency signals by amplifying said input radiofrequency signals and limiting their amplitude; and
   by a signal processing circuit, determining a phase shift of said input radiofrequency signals relative to said output radiofrequency signals, following said reduction or elimination of said amplitude modulation, and determining at least one quantity selected from the group consisting of a stroke volume and a cardiac output, using said phase shift.

2. The method of claim 1, wherein said reducing or eliminating amplitude modulation comprises maintaining a phase modulation of said input radiofrequency signals.

3. The method of claim 1, further comprising mixing the output radiofrequency signals and said input radiofrequency signals following said reduction or elimination of said amplitude modulation thereby to provide a mixed radiofrequency signal.

4. The method of claim 3, wherein said electronic circuitry is designed and configured to filter out a portion of said mixed radiofrequency signal so as to substantially increase a signal-to-noise ratio of a remaining portion of said mixed radiofrequency signal.

5. The method of claim 3, wherein said mixing comprises providing a radiofrequency sum and a radiofrequency difference.

6. The method of claim 5, further comprising filtering out said radiofrequency sum.

7. The apparatus of claim 6, wherein said filtering is by low pass filter characterized by a cutoff frequency of about 35 Hz.

8. The method of claim 4, wherein said signal-to-noise ratio is increased by at least 10 dB.

9. The apparatus of claim 1, wherein said input radiofrequency signals correspond to impedance value from about 25Ω to about 35Ω.

* * * * *